US012690907B2

(12) United States Patent (10) Patent No.: US 12,690,907 B2

Weiss, Jr. et al. (45) Date of Patent: Jul. 28, 2026

(54) PULSED FIELD ELECTROPORATION SYSTEMS AND METHODS

(71) Applicant: Aventix Medical Inc., Irvine, CA (US)

(72) Inventors: Raymond L. Weiss, Jr., Ocean Springs, MS (US); James H. Atkins, Jr., San Antonio, TX (US); Karthick Ramyan Mohan, Irvine, CA (US); John Ross Saunders, Edinburgh (GB); Jetmir Palushi, Irvine, CA (US)

(73) Assignee: Aventix Medical Inc., Laguna Hills, CA (US)

( * ) Notice: Subject to any disclaimer, the term of this patent is extended or adjusted under 35 U.S.C. 154(b) by 0 days.

(21) Appl. No.: 19/022,679

(22) Filed: Jan. 15, 2025

(65) Prior Publication Data

US 2025/0228596 A1 Jul. 17, 2025

Related U.S. Application Data

(60) Provisional application No. 63/621,443, filed on Jan. 16, 2024.

(51) Int. Cl.

| | |
|---|---|
| *A61B 18/00* | (2006.01) |
| *A61B 1/00* | (2006.01) |
| *A61B 1/227* | (2006.01) |
| *A61B 1/233* | (2006.01) |
| *A61B 1/24* | (2006.01) |

(Continued)

(52) U.S. Cl.

CPC .......... *A61B 18/00* (2013.01); *A61B 1/00009* (2013.01); *A61B 1/227* (2013.01); *A61B 1/233* (2013.01); *A61B 1/24* (2013.01); *A61B 90/90*

(2016.02); *A61N 1/0412* (2013.01); *A61N 1/327* (2013.01); *G16H 30/40* (2018.01); *G16H 40/63* (2018.01); *A61B 2018/00178* (2013.01); *A61B 2018/0022* (2013.01); *A61B 2018/00327* (2013.01); *A61B 2018/0091* (2013.01); *A61B 2018/00982* (2013.01)

(58) Field of Classification Search

CPC ........... A61B 2018/00327; A61B 2018/00988

See application file for complete search history.

(56) References Cited

U.S. PATENT DOCUMENTS

| | | | |
|---|---|---|---|
| 5,327,905 A | 7/1994 | Avitall | |
| 6,251,109 B1 * | 6/2001 | Hassett | .............. A61B 18/1492 606/49 |

(Continued)

FOREIGN PATENT DOCUMENTS

| | | | | |
|---|---|---|---|---|
| WO | WO-2022104158 A2 * | 5/2022 | ......... | A61B 18/1492 |
| WO | WO 2022/192459 A1 | 9/2022 | | |

OTHER PUBLICATIONS

Aycock et al., "A Theoretical Argument for Extended Interpulse Delays in Therapeutic High-Frequency Irreversible Electroporation Treatments, " IEEE Transactions on Biomedical Engineering, Jan. 5, 2021, 68(6):1999-2010.

(Continued)

*Primary Examiner* — Ronald Hupczey, Jr.

(74) *Attorney, Agent, or Firm* — Fish & Richardson P.C.

(57) ABSTRACT

An improved system described herein can include an expandable member (e.g., to temporarily dilate a targeted tissue) equipped with one or more Pulsed Field Electroporation (PFE) electrodes configured to cause localized and targeted PFE output at the targeted tissue.

23 Claims, 26 Drawing Sheets

(51) Int. Cl.

| | |
|---|---|
| *A61B 90/90* | (2016.01) |
| *A61N 1/04* | (2006.01) |
| *A61N 1/32* | (2006.01) |
| *G16H 30/40* | (2018.01) |
| *G16H 40/63* | (2018.01) |

(56) References Cited

U.S. PATENT DOCUMENTS

| | | | |
|---|---|---|---|
| 7,655,243 B2 | 2/2010 | Deem et al. | |
| 8,936,594 B2 | 1/2015 | Wolf et al. | |
| 9,072,597 B2 | 7/2015 | Wolf et al. | |
| 9,101,384 B2 | 8/2015 | Makower et al. | |
| 9,415,194 B2 | 8/2016 | Wolf et al. | |
| 9,943,361 B2 | 4/2018 | Wolf et al. | |
| 10,252,050 B2 | 4/2019 | Kreis et al. | |
| 10,456,185 B2 | 10/2019 | Wolf et al. | |
| 10,485,609 B2 | 11/2019 | Palushi et al. | |
| 10,610,675 B2 | 4/2020 | Deem et al. | |
| 10,722,282 B2 | 7/2020 | Wolf et al. | |
| 10,864,035 B2 | 12/2020 | Hester et al. | |
| 10,894,011 B2 | 1/2021 | Deem et al. | |
| 11,033,318 B2 | 6/2021 | Wolf et al. | |
| 11,167,125 B2 | 11/2021 | Moss et al. | |
| 11,241,271 B2 | 2/2022 | Wolf et al. | |
| 11,304,746 B2 | 4/2022 | Wolf et al. | |
| 11,311,721 B2 | 4/2022 | Ebbers et al. | |
| 11,324,543 B2 | 5/2022 | Waldstreicher et al. | |
| 11,419,671 B2 | 8/2022 | Townley et al. | |
| 11,547,473 B2 | 1/2023 | Townley et al. | |
| 11,576,719 B2 | 2/2023 | Townley et al. | |
| 11,666,378 B2 | 6/2023 | Townley et al. | |
| 11,679,077 B2 | 6/2023 | Deem et al. | |
| 11,766,286 B2 | 9/2023 | Wolf et al. | |
| 11,833,350 B2 | 12/2023 | Viswanathan et al. | |
| 11,883,091 B2 | 1/2024 | Townley | |
| 12,042,202 B1 | 7/2024 | Atkins et al. | |
| 12,082,863 B1 | 9/2024 | Atkins et al. | |
| 2002/0087208 A1* | 7/2002 | Koblish | A61B 18/1492 606/41 |
| 2006/0041277 A1 | 2/2006 | Deem et al. | |
| 2007/0267011 A1* | 11/2007 | Deem | A61N 1/05 128/200.23 |
| 2009/0254077 A1* | 10/2009 | Craig | A61B 18/1206 606/33 |
| 2011/0160514 A1 | 6/2011 | Long et al. | |
| 2012/0109122 A1 | 5/2012 | Arena et al. | |
| 2014/0052216 A1 | 2/2014 | Long et al. | |
| 2015/0080785 A1 | 3/2015 | Shantha | |
| 2018/0103994 A1 | 4/2018 | Fox et al. | |
| 2019/0247680 A1 | 8/2019 | Mayer et al. | |
| 2020/0046955 A1 | 2/2020 | Deem et al. | |
| 2020/0261149 A1 | 8/2020 | Shameli et al. | |
| 2021/0236816 A1 | 8/2021 | Waldstreicher et al. | |
| 2021/0315639 A1 | 10/2021 | Manucherhabadi et al. | |
| 2021/0378734 A1 | 12/2021 | Govari et al. | |
| 2022/0087739 A1 | 3/2022 | Paulushi et al. | |
| 2022/0218959 A1* | 7/2022 | Valls | A61B 5/6853 |
| 2022/0313353 A1 | 10/2022 | Paulushi et al. | |
| 2023/0057626 A1 | 2/2023 | Amaoua et al. | |

OTHER PUBLICATIONS

International Search Report and Written Opinion in International Appln. No. PCT/US2025/011706, mailed on Apr. 18, 2025, 17 pages.

* cited by examiner

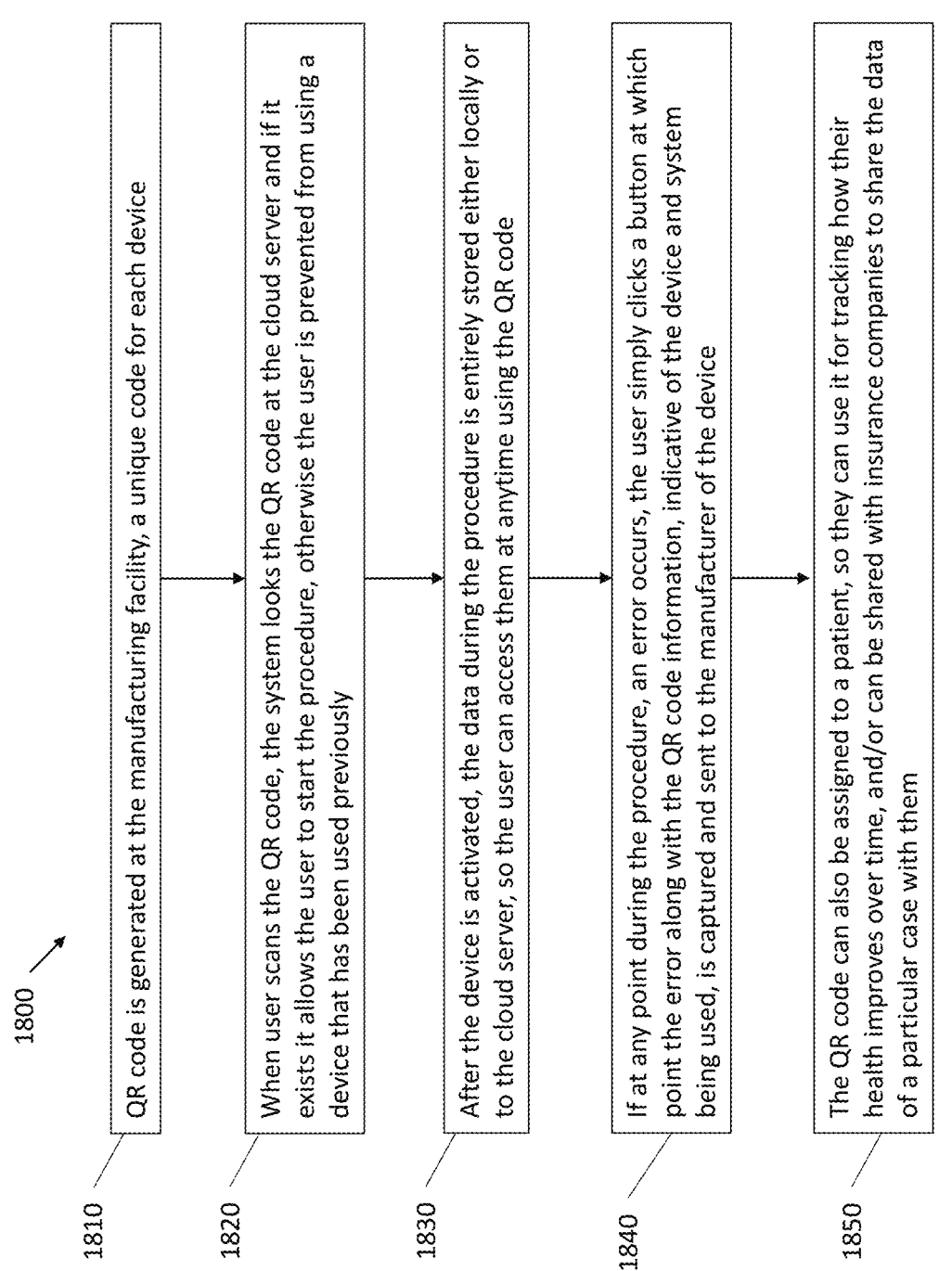

1800

1810  QR code is generated at the manufacturing facility, a unique code for each device 1820  When user scans the QR code, the system looks the QR code at the cloud server and if it exists it allows the user to start the procedure, otherwise the user is prevented from using a device that has been used previously 1830  After the device is activated, the data during the procedure is entirely stored either locally or to the cloud server, so the user can access them at anytime using the QR code 1840  If at any point during the procedure, an error occurs, the user simply clicks a button at which point the error along with the QR code information, indicative of the device and system being used, is captured and sent to the manufacturer of the device 1850  The QR code can also be assigned to a patient, so they can use it for tracking how their health improves over time, and/or can be shared with insurance companies to share the data of a particular case with them

FIG. 18

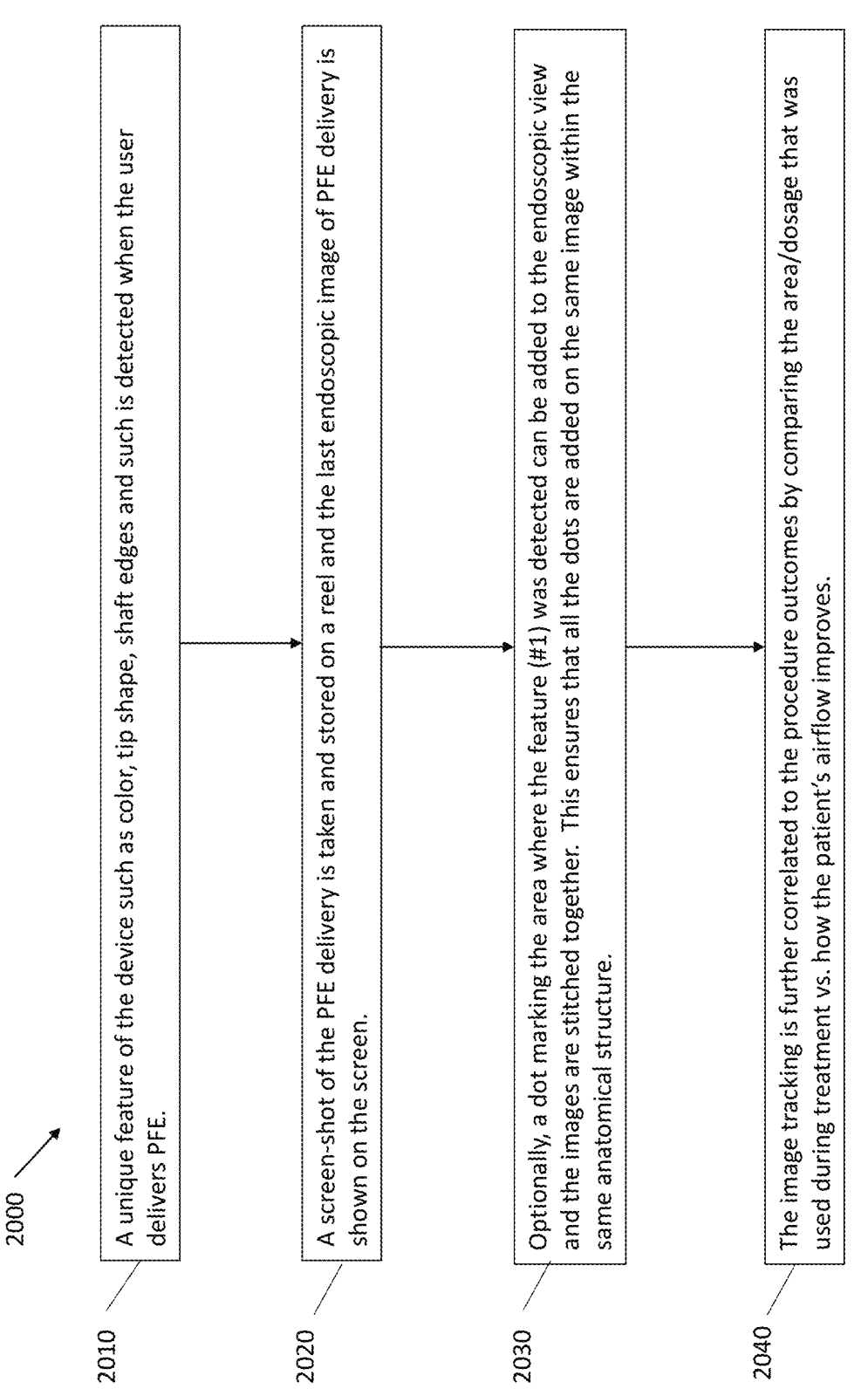

2010 A unique feature of the device such as color, tip shape, shaft edges and such is detected when the user delivers PFE.

2020 A screen-shot of the PFE delivery is taken and stored on a reel and the last endoscopic image of PFE delivery is shown on the screen.

2030 Optionally, a dot marking the area where the feature (#1) was detected can be added to the endoscopic view and the images are stitched together. This ensures that all the dots are added on the same image within the same anatomical structure.

2040 The image tracking is further correlated to the procedure outcomes by comparing the area/dosage that was used during treatment vs. how the patient's airflow improves.

FIG. 20

PULSED FIELD ELECTROPORATION SYSTEMS AND METHODS

This application claims the benefit of U.S. Provisional Patent Application No. 63/621,443 filed on Jan. 16, 2024, the contents of which are fully incorporated herein by reference.

TECHNICAL FIELD

This disclosure pertains to pulsed field electroporation (PFE) and dilation systems and methods. Some of the systems and methods include minimally invasive, expandable instrument balloons, and therapeutic PFE methods for use in the Eustachian tube (ET), paranasal sinuses, cochleae, olfactory system, and other Ear, Nose, and Throat (ENT) procedures.

BACKGROUND

The Eustachian tube is a narrow channel, approximately one-and-a-half-inches in length, connecting the middle ear with the nasopharynx (e.g., the upper throat area just above the palate) in the back of the nose.

The Eustachian tube functions as a pressure equalizing valve for the middle ear which is normally filled with air. When functioning properly the Eustachian tube opens for a fraction of a second about once every three minutes in response to swallowing or yawning. In so doing, it allows air into the middle ear to replace air that has been absorbed by the middle ear lining (mucous membranes) or to equalize pressure changes due to changes in altitude. Interference with this periodic opening and closing of the Eustachian tube may result in hearing impairment or other ear symptoms.

Obstruction or blockage of the Eustachian tube sometimes results in a negative middle ear pressure, which can cause the ear drum to retract. In adults this is usually accompanied by ear discomfort, a fullness or pressure feeling and may result in a hearing impairment and ringing in the ear (tinnitus). If the obstruction is prolonged, fluid may be drawn from the mucous membranes of the middle ear creating a condition known as serous otitis media (fluid in the middle ear). This condition can occur more often in children.

The paranasal sinus system is a grouping of four pairs of air-filled cavities. The maxillary sinuses (cheek sinuses) surround the nasal cavity, the frontal sinuses are above the eyes, the ethmoid sinuses are between the eyes, and the sphenoid sinuses are within the sphenoid bone at the center of the skull base under the pituitary gland. The paranasal sinuses are lined with respiratory epithelium, are joined to the nasal cavity via small orifices called ostia. The paranasal sinuses contain secretory tissue that can produce a large volume of mucus. This mucus normally flows from the sinuses in a specific pattern through the corresponding ostia.

The mucus membrane that lines the paranasal sinuses can become inflamed. This inflammation is known as sinusitis (or rhinosinusitis), and can be caused by various factors such as bacteria, viruses, allergies, anatomical abnormalities, etc. If the mucosa of one of the paranasal sinus ostia becomes inflamed, the passageway can become blocked, trapping mucus. Patients suffering from sinusitis can experience several symptoms or complications, such as headache, facial pain, toothache, cough, etc.

Sinusitis is typically classified as acute (infection lasting 4 or less weeks) or chronic (12 or more weeks). Many instances of acute sinusitis can be effectively treated with medication (e.g. antibiotics and/or oral steroids etc.). Chronic sinusitis sometimes requires a more invasive treatment option in which the paranasal passageways or affected sinuses are surgically accessed.

In one example of such surgical access, sinus balloon dilation can be performed on the sinus ostia (along the outflow tract that drains the sinus mucus into the nasal cavity) to open the blocked or partially blocked sinus ostia. The balloon is advanced into the sinus ostia, and after the balloon is in the right location, the user inflates the balloon resulting in the opening of the obstructed passage due to the mechanical forces exerted by the balloon thus allowing the mucus to drain freely from the sinus cavity.

Another form of sinus disease is when the mucosal lining of the paranasal sinuses becomes infected or thickened for long periods of time. The infected mucosal lining can extend into the ostia not allowing mucus to exit the sinus cavity. In addition, abnormal tissue such as polyps can grow within the sinus cavity which often needs to be removed since they disrupt the mucus flow within the sinus wall as well as cause congestion. In some cases, the sinus cavity can be dilated to allow the mucus to exit the sinus cavity and to provide access for polyp removal.

Factors such as injury to surrounding tissues, patient comfort, and post-procedure complications can impact treatments for sinus diseases and conditions. For example, an amount of time that a balloon needs to remain inflated in the Eustachian tube (e.g., 2 minutes) to complete a dilation procedure can cause some patients to experience discomfort due to tissue being subject to a mechanical expansion force—even when the patient is under local anesthesia.

A length of time required to do intra-sinus procedures can vary significantly, especially for those circumstances where the intra-sinus procedure includes removal of the tissue using rigid instrumentations referred to as Traditional Endoscopic Sinus Surgery (ESS), for purposes of treating sinus conditions. It can be difficult to use common energy modalities in sensitive structures such as paranasal sinuses, Eustachian tube, car cavity, and olfactory system because radiofrequency (RF), cryoablation (CA), and lasers use thermal energy to intentionally induce cell death, a process called "necrosis." Furthermore, using these ablative techniques can generate significant temperature change (e.g., significantly higher or lower than the normal body temperature) at the targeted tissue arca, which can increase the risk of unintended injury to healthy tissue in certain cases. For example, if RF ablation energy is delivered in a targeted tissue area, this targeted tissue area can be at higher risk of severe crusting or scab formation as compared with pulsed field electroporation (PFE) treatments. Also, these thermal ablation instruments (e.g., RF, CA, and lasers) may cause complications during intra-sinus procedures where the thermal profile may extend their ablative effects beyond the targeted tissue type and into other types of tissues and adjacent structures. For example, during such necrosis-inducing energy delivery, extension of the zone of ablative effects past the targeted tissue may lead to unintended damage of critical structures such as blood vessels that are proximate to the active electrode or are exposed to elevated temperatures.

The olfactory system is a sensory system that contributes to the sense of smell. For example, the olfactory system involves a complex network including olfactory receptors located in the nasal cavity. When odor molecules enter the nose, these molecules can bind to olfactory receptors. Because olfactory nerve fibers represents specialized neurons capable of detecting many different chemical compounds, odor molecules of varying chemical structure can bind to olfactory receptors in a way that causes an electrical response in olfactory nerve fibers. This binding can trigger a series of neural signals that can be transmitted to the olfactory bulb, a structure at the base of the brain that can process these signals and relay the signals to other brain regions, including the limbic system, which is involved in emotion and memory. For example, olfactory nerve fibers can connect olfactory receptors to the olfactory bulb so that olfactory receptors can send signals to the olfactory bulb through the olfactory nerve fibers. Connections between the olfactory receptors and the brain can evoke strong memories or feelings relating to certain smells.

In some cases, olfactory receptors and/or tissue surrounding the olfactory nerve fibers can be damaged over time in a way that causes abnormal excitation or inhibition of the olfactory nerves. This condition can affect a sense of smell, leading to issues such as a reduced ability to detect odors (e.g., hyposmia), a complete loss of smell (e.g., anosmia), or a distortion of smell (e.g., parosmia). Because the sense of smell can be linked to taste, olfactory diseases can significantly impact quality of life. For example, olfactory diseases can impact appetite and safety because an impaired sense of smell can lead to a failure to detect smoke or spoiled food, for example. Diagnosis of olfactory diseases and conditions can involve clinical evaluation, smell tests, and sometimes imaging studies to identify underlying causes.

Another sensory system is the auditory system, which contributes to the sense of hearing. The auditory system includes the cochlea, a spiral-shaped, fluid-filled structure located in the inner ear. The cochlea contributes to the sense of hearing by converting mechanical sound waves into electrical signals that are transmitted to the brain. For example, the cochlea is a snail shell-shaped container that includes thousands of hair cells within fluid. These hair cells represent sensory receptors that can convert sound vibrations into electrical signals. For example, mechanical sound waves cause waves to propagate through the fluid within the cochlea which mechanically stimulate the hair cells. Based on these mechanical movements, the hair cells can generate electrical signals. The electrical signals can be transmitted to the auditory nerve and sent to the brain. The brain processes these signals in a way that causes a sense of hearing. The cochlea can be divided into three chambers including the scala vestibuli, the scala media, and the scala tympani. Each of these three chambers can play an important role in mechanics of hearing. Movement of fluid within these chambers caused by mechanical sound waves can stimulate hair cells within the cochlea, allowing a perception of a wide range of frequencies. Damage to the cochlea can result from various factors, leading to hearing loss. Common causes of damage to the cochlea include prolonged exposure to loud noises, which can destroy hair cells and aging, which can lead to gradual loss of these cells. In some cases, infections, medications (e.g., ototoxic drugs), and physical trauma can harm the cochlea. When hair cells within the cochlea are damaged or lost, an ability to convert sound waves into electrical signals diminishes, resulting in conditions such as sensorineural hearing loss. Because cochlear hair cells do not regenerate, it can be difficult to treat hearing loss conditions resulting from damage to cochlear hair cells.

SUMMARY

Some embodiments described herein can include an improved system that is configured to access and engage a targeted tissue (e.g., for dilation) along any of the Eustachian tube, paranasal sinuses, and other ear, nose, and throat sites while contemporaneously delivering pulsed field electroporation (PFE) to the targeted tissue. In particular implementations, the system can include an improved dilation instrument (e.g., a dilation balloon to temporarily dilate a Eustachian tube or an ostia of a paranasal sinus) that is equipped with PFE electrodes configured to cause localized and targeted PFE at the dilated tissue. As described in additional detail below, some embodiments of the system can cause localized PFE by using an electric field, which is applied to the targeted tissue in rapid bursts to cause irreversible electroporation (IRE). This induces cell membrane destabilization to cause a particular type of cell death called "apoptosis." As such, these embodiments of the PFE instruments can treat the targeted tissue to cause apoptosis, a cell death process that is similar to a natural and controlled part of anatomical growth or development, while avoiding the thermal ablation energy (e.g., from RF, CA, or laser ablation) that induces the above-described necrosis. Optionally, the PFE system described herein can be configured to output PFE in a manner that selectively targets the predetermined tissue type to be treated, which can thereby reduce cell inflammation and avoid complications associated with traditional thermal ablation energy (from RF, CA, and lasers) with ablative effects extended outside of the targeted treatment zone.

According to some embodiments described herein, an improved sinus dilation system may integrate PFE to more effectively treat the Eustachian tube or paranasal sinus while reducing the likelihood of injuring the non-targeted tissue (as may occur with the necrosis-inducing ablation instruments, such as RF ablation, CA, or laser ablation tools). For example, the improved system described herein can be configured to output PFE to selectively and non-thermally open the cell pores in the targeted tissue to induce apoptosis which may reduce the likelihood of damaging non-targeted tissue such as blood vessels. In many cases, the improved system can accomplish such treatment without the use of general anesthesia on the patient, thereby providing added convenience for both the user and the patient. For example, the improved system can accomplish such treatment using a (optional) topical anesthetic at the treatment site. Optionally, some versions of the improved sinus dilation system with integrated PFE may also be used to more effectively deliver drugs, such as steroids, to the targeted tissue. A method of tracking the treated anatomical space and correlating the treatment spaces to outcomes is also disclosed.

In some options described herein, the system can be configured to deliver PFE for one or both of two distinct effects to the targeted tissue. The first type, as described above, is related to irreversible electroporation (IRE) which kills the cells by the process of apoptosis, and the second type is reversible electroporation (RE) where the cell membrane pores are enlarged so that large molecule drugs, such as steroids, can permeate through the cell membrane but there is no cell apoptosis, or cell death.

In various embodiments described below, the waveform of the PFE system can be optimized to also modulate the nerves located proximate to the electroporation electrode of the PFE device. The neurostimulation effect is desired so it resets the nerve activity, thus resulting in normal nerve signaling communication of the nerve. Nerve activity can be modulated to stimulate cell growth and repair, using PFE specifically to regenerate hair cells (e.g., cochlear hair cells). Optionally, this method of PFE can add benefits in such a way that the nerve activity may be modulated to potentially reduce neuralgia. In some cases, nerve stimulation effects can be excitatory or inhibitory. Excitatory nerve stimulation, for example, involves increasing nerve stimulation activity and inhibitory nerve stimulation involves decreasing nerve stimulation activity. To treat diseases such as chronic rhinosinusitis (CRS), chronic rhinitis (CR), and others, the nerve activity can be reduced (e.g., inhibited) so the mucus formation is reduced to normal levels. To treat other diseases such as hearing loss or types of migraines, nerve signaling can be increased (e.g., excited) to regenerate healthy tissue and/or nerve fibers.

Some embodiments described herein include a system that comprises a nasal dilation instrument. The nasal dilation instrument may include a handle, an elongated shaft extending distally from the handle, and a treatment tip at a distal end portion of the elongated shaft. Optionally, the treatment tip may have a dilation balloon and a PFE electrode such that the treatment tip is configured to deliver PFE from the PFE electrode at nasal tissue dilated by the dilation balloon.

Further embodiments of a system described herein can include a PFE delivery instrument configured to access targeted tissue of an car, nose, or throat site. The PFE delivery instrument may include a treatment tip with an expandable PFE electrode to deliver PFE at the targeted tissue.

Some embodiments described herein include a method that comprises inserting an elongated shaft of a PFE delivery instrument into an car, nose, or throat site such that an adjustable PFE electrode of a treatment tip at a distal end of the PFE delivery instrument is adjacent to a targeted tissue. The method may optionally include adjusting the PFE electrode relative to the elongated shaft to compress the PFE electrode against the targeted tissue. Additionally, the method may include activating a PFE generator of a control console connected to the PFE delivery instrument to output an electric field in a predefined pattern from the PFE electrode to induce at least one of irreversible electroporation (IRE) at the targeted tissue and reversible electroporation (RE) at the targeted tissue.

A number of embodiments herein include a system that comprises a pulsed field electroporation (PFE) generator configured to output pulsed PFE. The system may also include a touchscreen interface coupled to the generator configured to receive user input to control PFE characteristics output from the generator. Optionally, the system can include a PFE delivery instrument including an elongated shaft and a PFE electrode that is adjustable relative to the elongated shaft to deliver the PFE from the PFE generator to at least one of a Eustachian tube, a paranasal sinus, a middle car, mastoid tissue, and an intra-sinus cavity.

Further embodiments described herein include a method of using a pulsed field electroporation (PFE) instrument. The method can include advancing a treatment tip of a PFE instrument into a subject such that a PFE electrode along the treatment tip is proximate to a targeted site. Optionally, the method can include outputting a PFE waveform from the PFE electrode of the treatment tip to induce apoptosis at the targeted site.

Additional embodiments described herein include a pulsed field electroporation (PFE) method of treating targeted tissue of an ear nose, or throat—preferably, without application of general anesthesia. The method can include compressing a PFE electrode against the targeted tissue while outputting a PFE waveform from the PFE electrode.

Some embodiments described herein include a method of delivering a pulsed field electroporation (PFE) waveform to targeted tissue of an ear nose, or throat—preferably, without inducing necrosis at the targeted tissue. The method can include advancing a treatment tip of a PFE instrument such that a PFE electrode along the treatment tip is proximate to targeted tissue of an ear nose, or throat. Optionally, the method can include outputting a PFE waveform from the PFE electrode of the treatment tip to induce apoptosis at the targeted tissue.

Further embodiments described herein can include a system comprising a pulsed field electroporation (PFE) delivery instrument configured to both dilate targeted tissue and to output PFE from a PFE electrode proximate to the targeted tissue.

BRIEF DESCRIPTION OF THE DRAWINGS

FIG. 18 shows a flowchart of a process of using the instrument of FIG. 17 with the PFE console of FIGS. 1-2, in accordance with some embodiments.

FIG. 20 shows a flowchart of a process of using the system of FIG. 1 with the treatment tracking algorithm of FIG. 19, in accordance with some optional methods of implementation.

DETAILED DESCRIPTION

Figure 1:
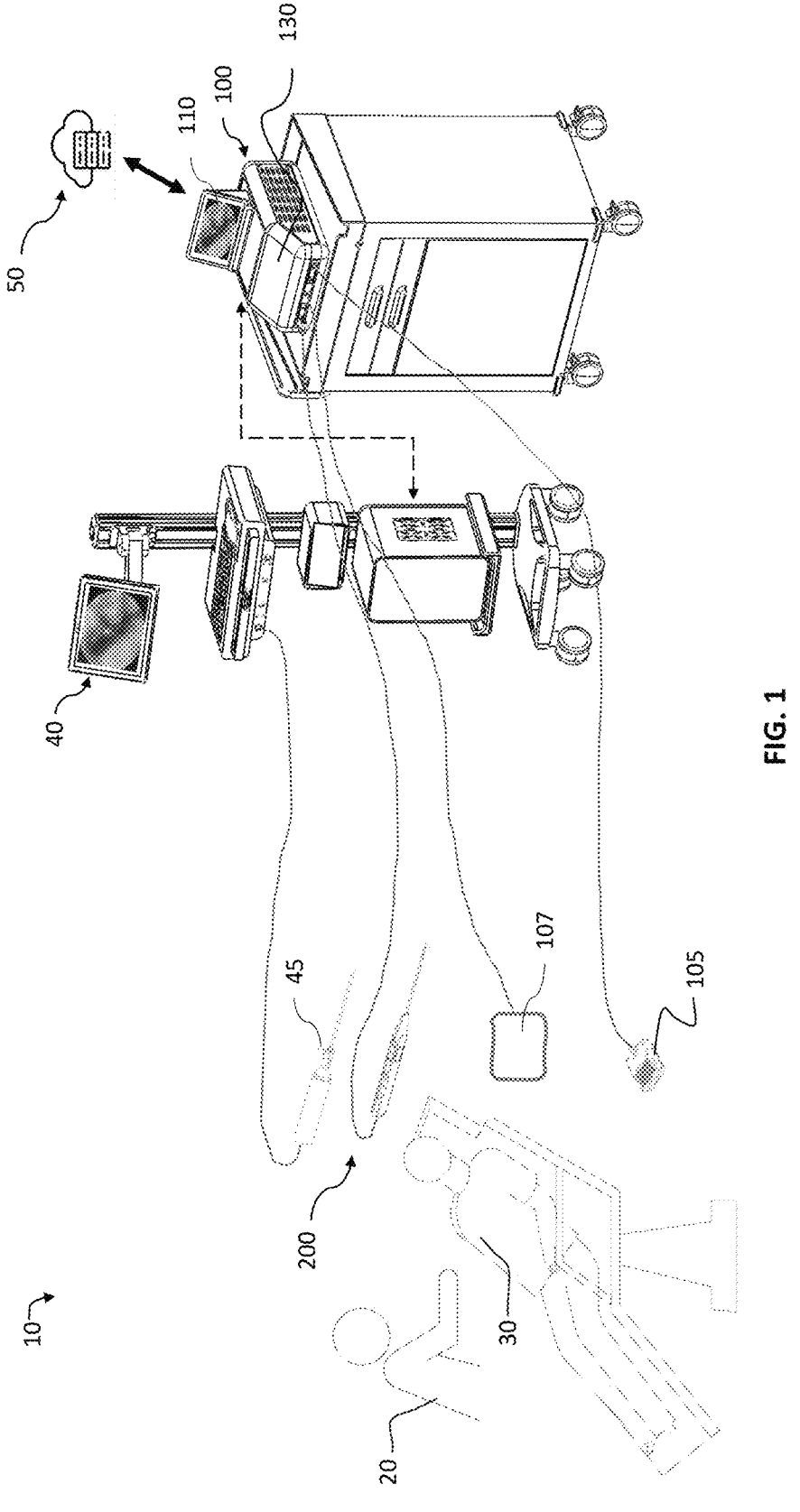
FIG. 1 shows a perspective view of a system for treating car, nose, or throat tissue, in accordance with some embodiments.
Figure 2:
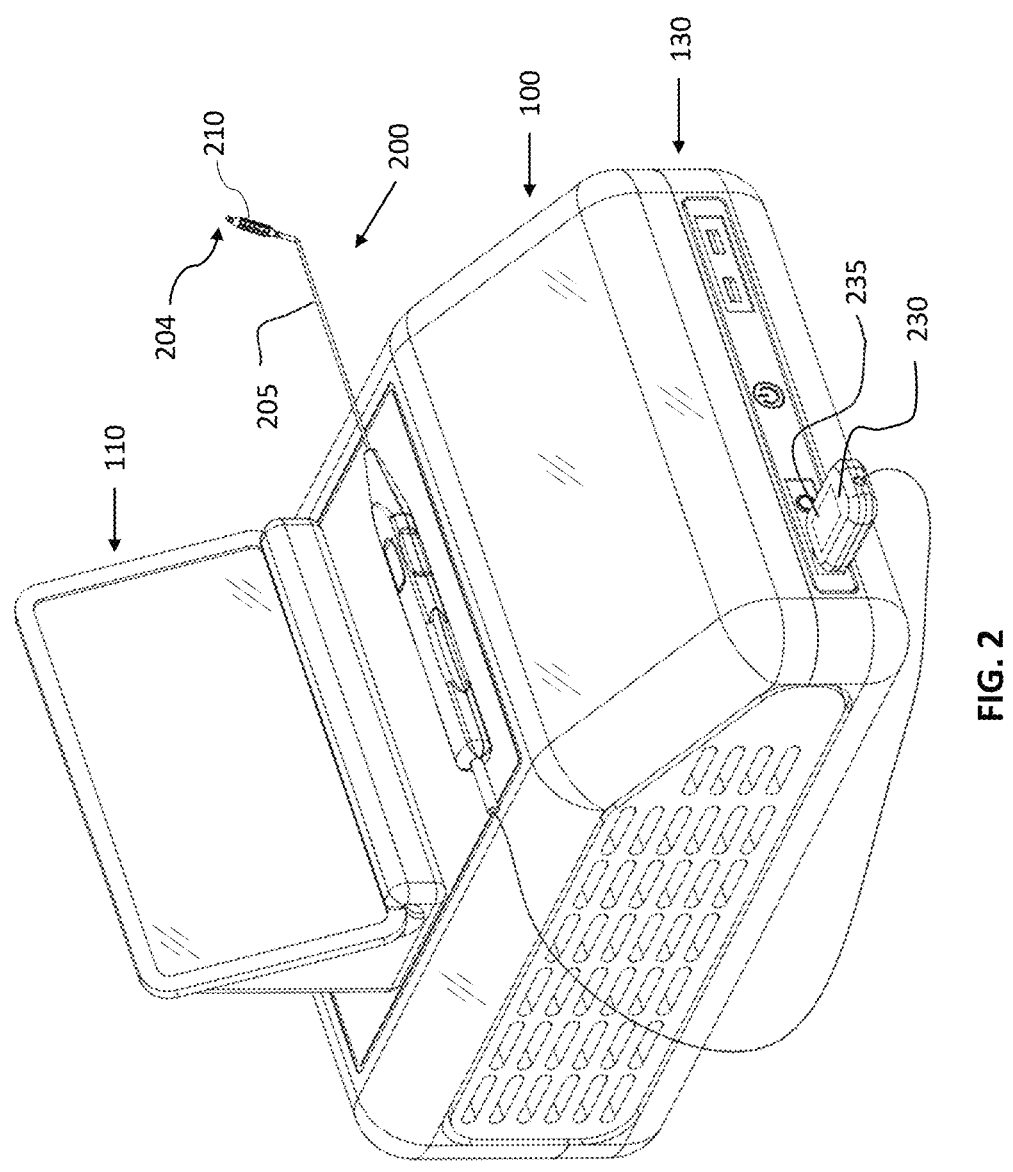
FIG. 2 shows a perspective view of a PFE console and instrument of the system of FIG. 1.
Figure 3:
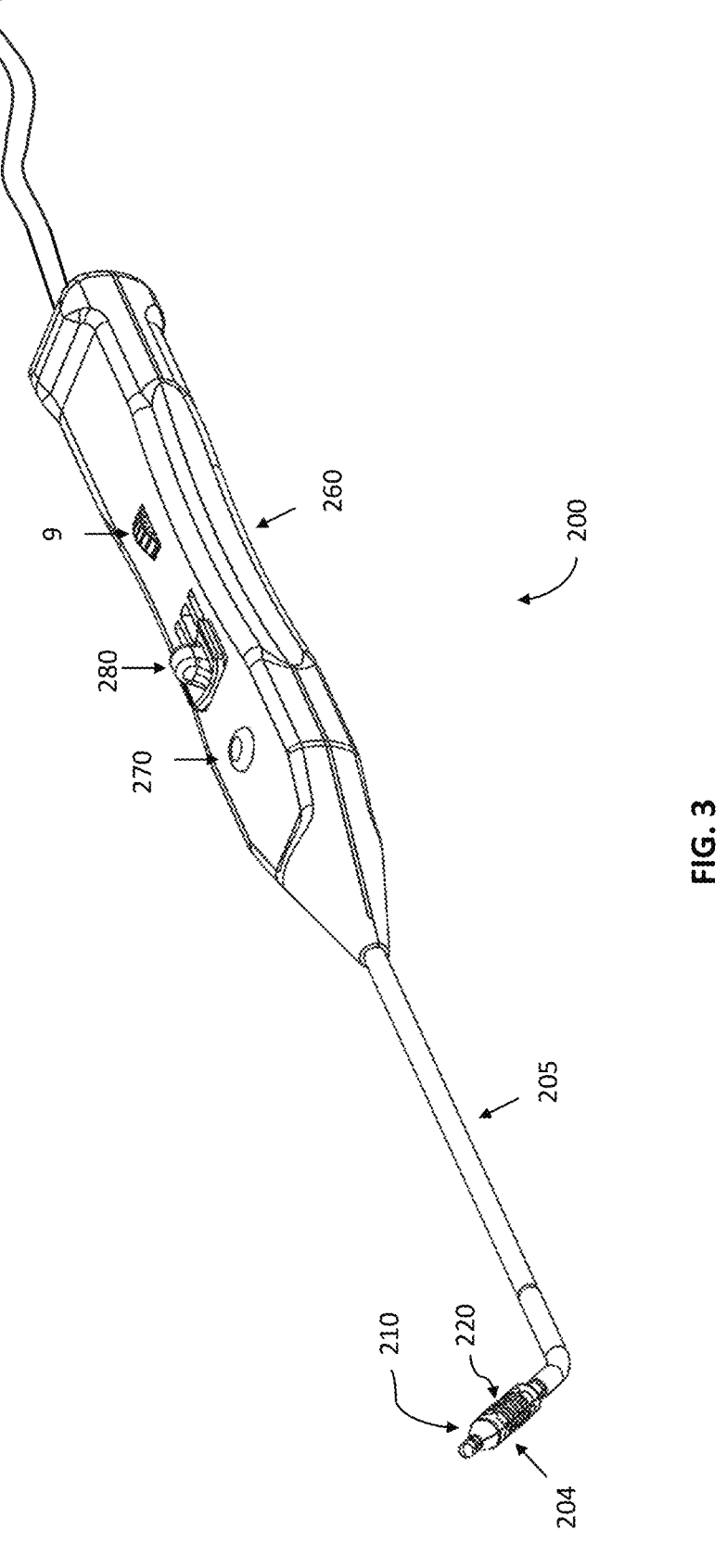
FIG. 3 is perspective view of the instrument of FIG. 2.

Referring now to FIGS. 1-3, some embodiments of a system 10 for treating car, nose, or throat tissue can include a Pulsed Field Electroporation (PFE) control console 100 and a PFE delivery instrument 200, which can be configured to access and engage a targeted tissue (e.g., for dilation) along any of the Eustachian tube, paranasal sinuses, and other car, nose, and throat sites while contemporaneously delivering Pulsed Field Electroporation (PFE) to the targeted tissue. For example, a user 20 can guide the instrument 200 into a nose of a patient 30 and then activate the PFE control console 100 so that PFE may be used to treat a swollen or diseased tissue of the sinus ostia, Eustachian tube, intracranial tissue, and intra-sinus tissue proximate thereto. The control console 100 includes a generator 130 configured to output a PFE signal and a user interface 110. The instrument 200 is removable attachable to the control console 100 such that the control console is configured to be reused with multiple instruments 200 over time and can store and transmit information about those multiple instruments (detailed below). Additionally, the instrument 200 includes a treatment tip 204 positioned along a distal end portion or an elongated shaft 205 ending and configured to output PFE via a one or more electrodes (such as mesh electrodes or needle-like electrodes, as detailed below). Optionally, the treatment tip 204 can be equipped with an expandable member 210, such as one or more dilation balloons, so as to engage the PFE electrode(s) against a targeted tissue of the sinus ostia, Eustachian tube, intracranial tissue, intra-sinus tissue, or the like. As described in more detail below, the system 10 can further include a footswitch 105 (for selective activation by the user 20), a disposable ground electrode pad 107 (for temporary adhesion to the patient 30), an endoscope system 40 (for medical imaging during delivery and use of the instrument 200), and a cloud server system 50 (for remote communication with the control console 100).

In use, the instrument 200 is advanced to the diseased tissue which may need to be treated, then if dilation is required, the expandable member 210 (e.g., a dilation balloon in this example) is advanced and inflated resulting in the opening of the anatomical space. Next the PFE electrode 220 (FIG. 3) is activated to treat the targeted tissue via electroporation, which is controlled by the console 110 (FIG. 1) to achieve a predetermined electric field applied to the targeted tissue in a rapid pattern that induces cell membrane destabilization at the targeted tissue. Optionally, the PFE electrode 220 may work in conjunction with the grounding electrode pad 107 (FIG. 1) mounted to the patient's body. Additionally, as described in more detail below, the instrument 200 can be advanced to the targeted anatomical space under medical imaging, for example using the endoscope system 40 (FIG. 1) including a handheld endoscope instrument 45 configured to be handled by the user simultaneously with the use of the PFE delivery instrument 200. In some circumstances, the PFE electrode 220 of the instrument 200 may be used without dilation especially in areas such as intra-sinus cavity, intracranial tissue, and others that may not need dilation. The PFE generator of the control console 100 can be activated by pressing a user interface button 270 of the instrument 200 (FIG. 3), or optionally, using the footswitch 105 (FIG. 1). As detailed below, in some embodiments, the control console 100 may be configured to selectively enable the PFE output from the generator 130 in response to an authorized instrument 200 being connected therewith, for example, by capturing a QR code or identifier 235 at a connector 230 of the instrument 200 (refer also to FIG. 17 below). The control console 100 may communicate (e.g., via a wired or wireless connection to the internet) with the cloud server system 50 to validate the identifier 235 of the instrument, as well as transmit treatment data from the control console 100 to the cloud server indicative of the use of that particular instrument 200 (having the identifier 235) with the particular patient 30 on that date.

Figure 4:
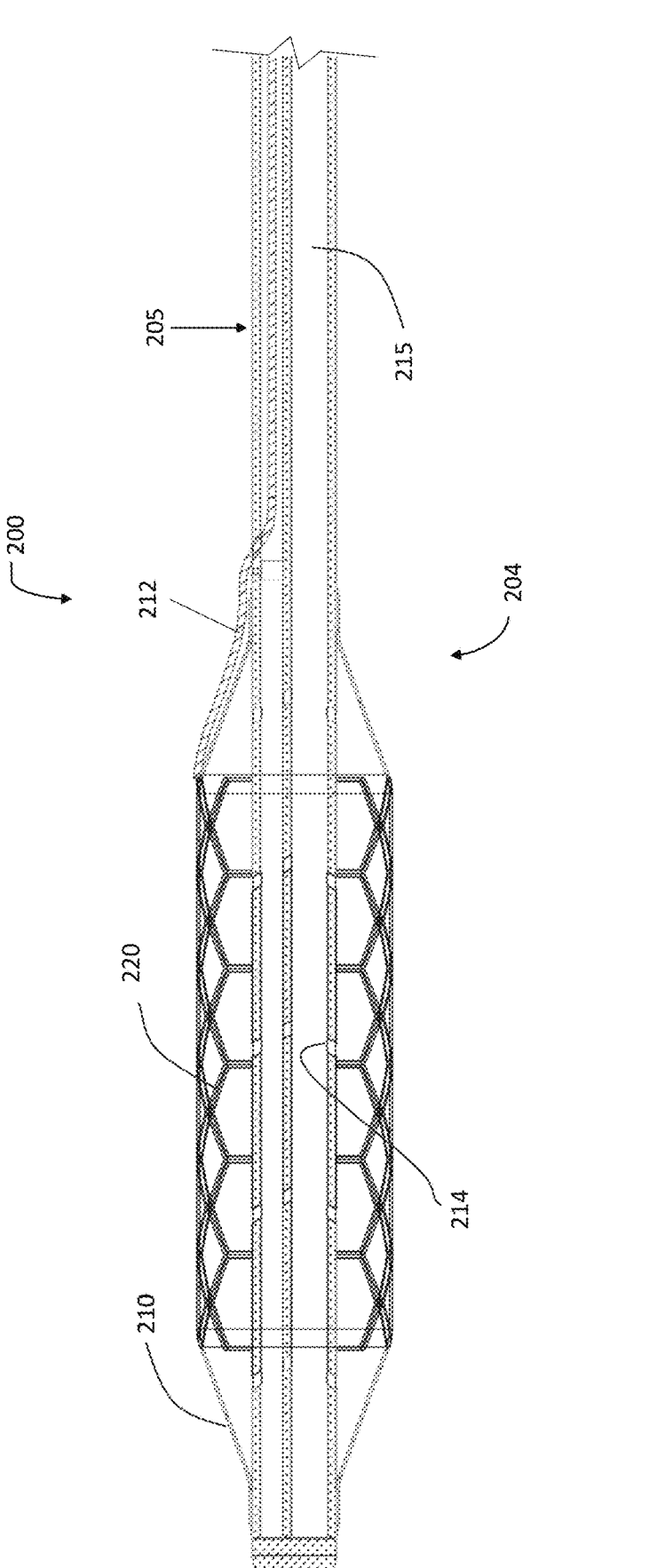
FIG. 4 shows a side view of a distal portion of the instrument of FIG. 3, in accordance with some embodiments.

Referring now to FIGS. 3-4, some embodiments of the PFE delivery instrument 200 may include a control handle 260 and the elongated shaft 205 extending distally from a distal end of the control handle 260. In this embodiment, the elongated shaft 205 is a catheter shaft sized to extend into a nasal passage such that a treatment tip 204 of instrument 200 extends to engage with targeted tissue, such as paranasal sinuses, Eustachian tube, and others. The treatment instrument handle 260 may include multiple user interface actuators, such as the PFE activation button 270, a rotation actuator 280 to urge rotation of the tip 204 clockwise and counterclockwise (e.g., motion in a radial plane), and an articulation actuator 290 to urge articulated motion of the tip 204 in upward and downward directions (e.g., motion in an axial plane). Preferably, at least a portion of the elongated shaft 205 may be made of malleable material in a region proximal to the treatment tip 204, in such a way that this portion of the shaft 205 can be bent during use.

In this depicted embodiment, the treatment tip 204 includes a PFE output electrode 220 in the form of a metallic mesh (or stent) structure, which is configured to surround the dilation balloon 210 expand and retract with the dilation balloon 210. As previously described, the dilation balloon 210 is selectively expandable to dilate one or more constricted anatomical passages prior to outputting the PFE from the electrode 220 (and to maintain the dilation during the out of the PFE from the electrode 220). For example, the balloon 210 can be inflated by infusing an inflation fluid through an inflation channel 215 of the elongated shaft 205. When the inflation fluid reaches the treatment tip 204 of the instrument 200, inflation fluid passes through the balloon ports along a circumferential wall of the inflation channel 215 to expand the balloon 210 to a selected pressure. Optionally, the control console 100 can manage the supply of inflation fluid through the inflation channel 215 (to expand or retract the balloon in a controlled manner) in response to actuation of a user interface button along the handle 260 (or, alternatively, a footswitch 105). The PFE electrode 220 is position along an exterior of the balloon 210 and expands with the balloon 210 during inflation. After the balloon dilation has been achieved, the balloon 210 is maintained in the inflated condition so the PFE electrode 220 is in its expanded state and engages with the targeted tissue, at which point the user can selectively activate (e.g., using the button 270) the generator 130 to output the PFE from the electrode 220 into the tissue. In this embodiment, the electrode 220 is connected to the instrument connector 230 (FIG. 2) via a conductive wire 212 for an electrical connection between the generator 130 and the electrode 220 for PFE delivery. Optionally, the mesh electrode 220 may output PFE delivery without a dilation balloon 210, in which case the mesh electrode 220 may be a self-expanding structure (e.g., a stent that can be selectively expanded and retracted via the handle 260) comprising an electrically conductive material such as nitinol, thus resulting in the mesh electrode 220 making contact with the tissue to be treated with PFE without expansion of a balloon at the treatment tip 204.

Figure 5D:
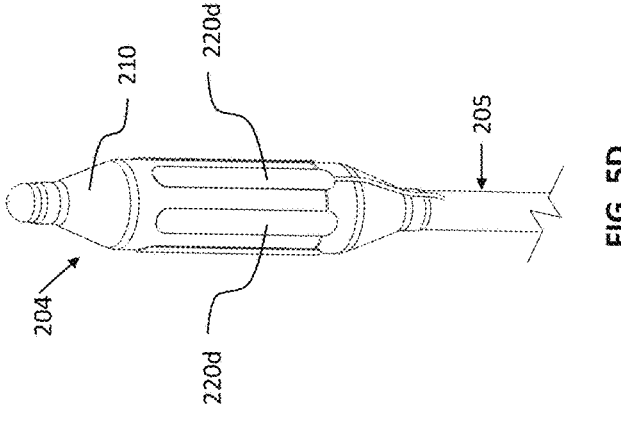
FIGS. 5A-5D show perspective views of distal portions of optional instruments for the system of FIG. 1, in accordance with some embodiments.
Figure 5C:
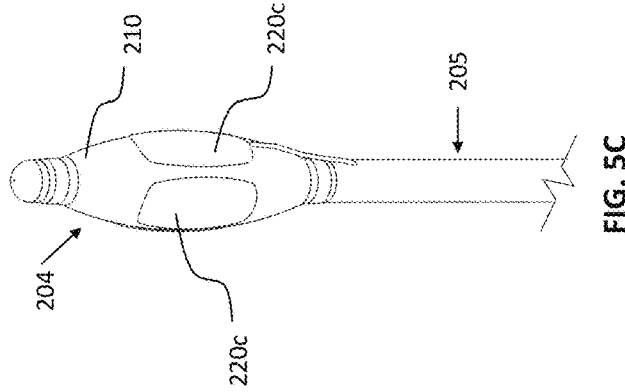
Figure 5B:
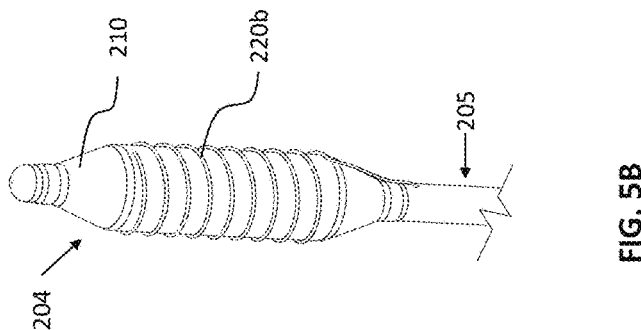
Figure 5A:
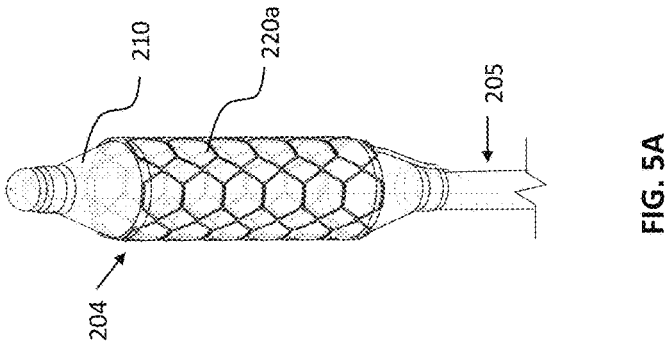

Referring now to FIGS. 5A-5D, various implementations of the PFE delivery instrument 200 can optionally include different electrode geometries and components. For example, as shown in FIG. 5A (which is consistent with FIGS. 3-4), the treatment tip 204 of the instrument 200 includes a mesh PFE electrode 220a. In some examples, the electrode 220a depicted in FIG. 5A is an example of the electrode 220 depicted in FIGS. 3 and 4. As shown in FIG. 5B, some implementations of the instrument 200 can include a spiral PFE electrode 220b that surrounds the balloon 210. Alternatively, some implementations of the instrument 200 can include a surface PFC electrodes 220c (FIG. 5C) or 220d (FIG. 5D) mounted along an exterior of the balloon 210, which can have corresponding electrical leads extending to a proximal end for purposes of achieving a bipolar output (e.g., eliminating the need of a ground pad 107 as depicted in FIG. 1). In these embodiments, the balloon 210 shown here can be used to compress any of the electrodes 220a-220d against targeted tissue for delivering PFE. In some cases, the balloon 210 can be used for dilation of the tissue prior to the delivery of PFE (and then full or partially collapsed). The electrodes 220a, 220b shown in FIGS. 5A-5B may be fixedly mounted to the exterior surface of the balloon 210, for example, where the balloon 210 will be inflated to a predetermined pressure and size. The electrodes 220c, 220d shown in FIGS. 5C-5D may each comprise an electronic circuit directly fixed onto the exterior surface of the balloon 210 such that the electrodes 220c, 220d can be adjusted to a position engaged against with the tissue (upon expansion of the balloon 210). The options for the electrode 220a or 220b in FIGS. 5A-5B can be particularly useful when the PFE can be delivered over an entire circumferential area surrounding the balloon 210 where the electrode 220a or 220b contacts with the tissue. The options for the electrode 220a or 220b in FIGS. 5C-5D can be particularly useful, for example, in procedures in which the user can selectively activate each electrode 220c or 220d in isolation (directional PFE delivery) or can deliver PFE in a bipolar approach (where one electrode 220c or 220d is a positive polarity and another of the similar electrode 220c or 220d is of negative polarity, and they alternate as the PFE is delivered).

Figures 6A, 6B, 6C:
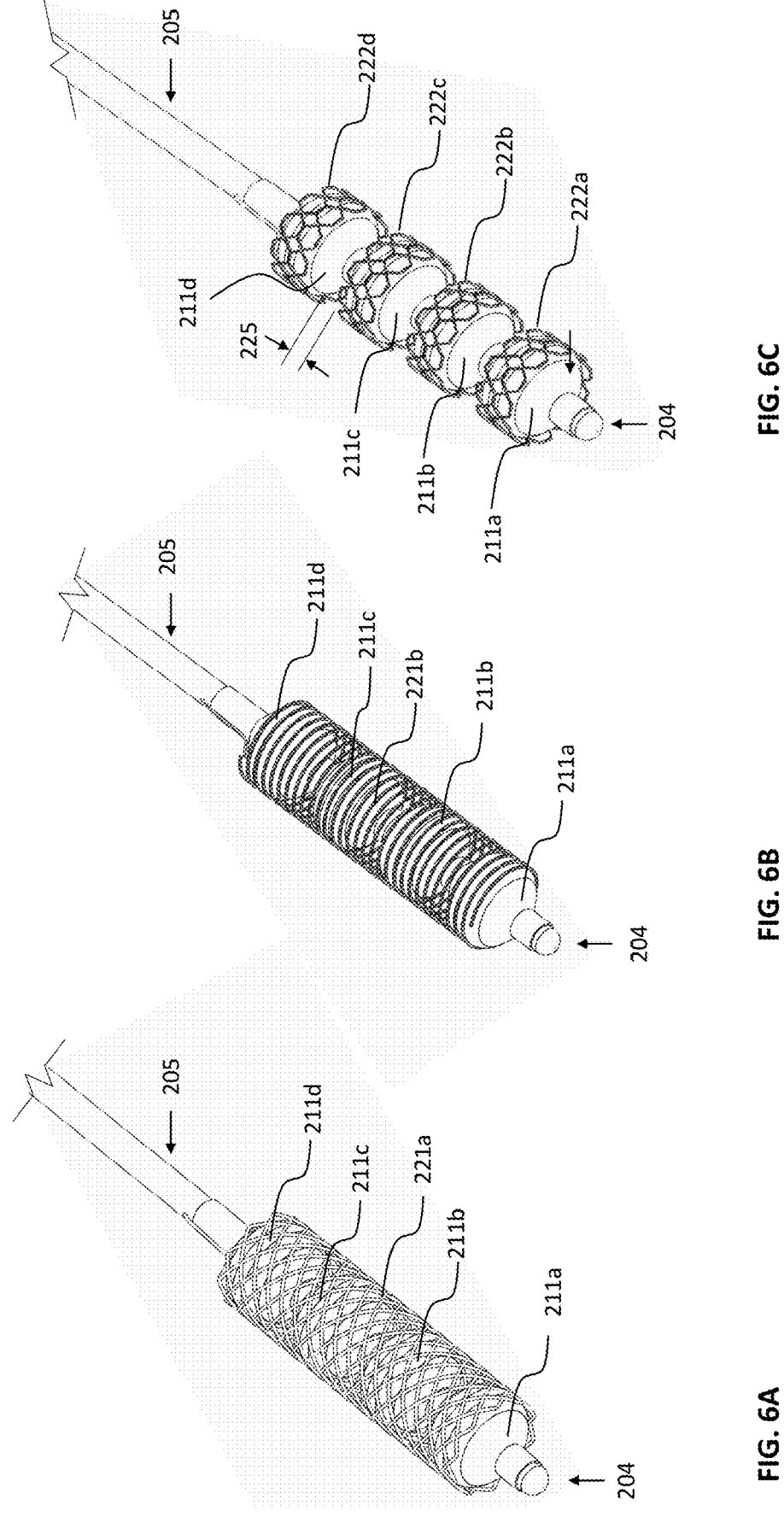
FIGS. 6A-6C show perspective views of distal portions of optional instruments for the system of FIG. 1, in accordance with some embodiments.

Referring now to FIGS. 6A-6C, various implementations of the PFE delivery instrument 200 can optionally include multiple balloons along the treatment tip 204, and such multi-balloon implementations can provide different electrode geometries and components. For example, as shown in FIG. 6A, the treatment tip 204 of the instrument 200 can include a series of inflatable dilation balloons 211a-211d (collectively, "balloons 211") that are positioned adjacent one another along the treatment tip 204, with all of the balloons 211 surrounded by the above-described mesh PFE electrode 221A. In some cases, mesh PFE electrode 221A is similar to the mesh PFE electrode 220 of FIGS. 3-4 and the mesh PFE electrode 220a of FIG. 5A. Mesh PFE electrodes can define a variety of patterns. For example, as depicted in FIG. 6A, mesh PFE electrode 221a includes a plurality of struts that define a plurality of diamond-shaped openings. As depicted in FIG. 5A, mesh PFE electrode 220a includes a plurality of struts that define a plurality of diamond-shaped openings and a plurality of hexagon-shaped openings. the mesh PFE electrodes of this disclosure are not limited to the patterns depicted in FIGS. 5A and 6A. Mesh PFE electrodes can define patterns not depicted in FIGS. 5A and 6A.

As shown in FIG. 6B, the treatment tip 204 of the instrument 200 can include the series of inflatable dilation balloons 211 that are positioned adjacent one another along the treatment tip 204, with all of the balloons 211 surrounded by the above-described spiral PFE electrode 220b (similar to FIG. 5B). As shown in FIG. 6C, the treatment tip 204 of the instrument 200 can include the series of inflatable dilation balloons 211 that are positioned adjacent one another along the treatment tip 204, with each individual balloon of balloons 211 being surrounded by a corresponding mesh PFE electrode of mesh PFE electrodes 222a-222e (collectively, "electrodes 222"). For example, the treatment tip 204 of FIG. 6C includes four balloons 211 and four corresponding mesh PFE electrodes 222, with mesh PFE electrode 222a surrounding balloon 211a, mesh PFE electrode 222b surrounding balloon 211b, mesh PFE electrode 222c surrounding balloon 211c, and mesh PFE electrode 222d surrounding balloon 211d.

In these depicted embodiments of FIGS. 6A-6C, the balloons 211 are spaced apart from one another along the shaft 205 by a balloon separation distance 225 (FIG. 6C). As previously described, for implementations where the treatment tip 204 includes multiple PFE electrodes, such as the multiple electrode configurations in n FIGS. 5C-5D, and 6C, the instrument 200 can be configured to provide a bipolar output of PFE in a manner that further optimizes the directionality or local surface concentration of PFE delivery because the PFE output is delivered between the neighboring electrodes 220c, 220d, or 222 at the treatment tip 204 of the instrument 200. In other circumstances, the multiple electrode configurations can be activated in a monopolar manner (e.g., used in conjunction with a ground electrode pad 107 (FIG. 1)) so as to provide a greater depth of the tissue treatment zone.

Figure 7B:
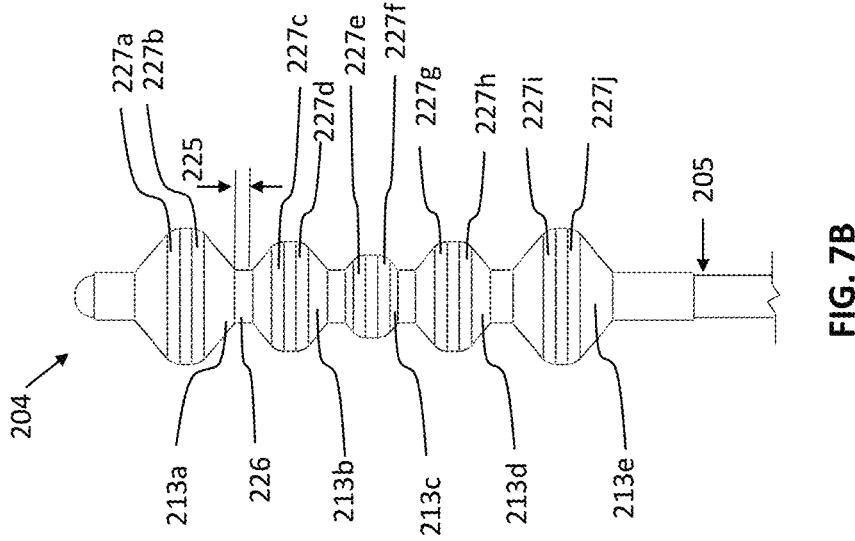
FIGS. 7A-7B show side views of multi-balloon configurations of distal portions of optional instruments for the system of FIG. 1, in accordance with some embodiments.
Figure 7A:
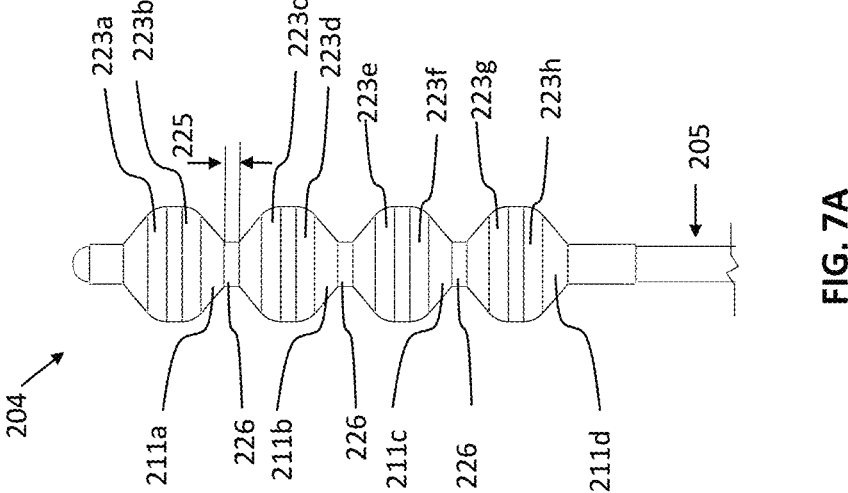

Referring now to FIGS. 7A-7B, some implementations of the PFE delivery instrument 200 can optionally include multiple balloons along the treatment tip 204, and such multi-balloon implementations can each include surface-mounted PFE electrodes. For example, as shown in FIG. 7A, the treatment tip 204 of the instrument 200 can include a series of inflatable dilation balloons 211 similar to those previously described in connection with FIGS. 6A-6C (e.g., four balloons 211 of the same size and expanded shape that are spaced apart by a separation distance 225 to expose intermediate shaft portions 226). As depicted in FIG. 7A, each of the balloons 211 can be equipped with multiple surface-mounted PFE electrodes of a set of surface-mounted PFE electrodes 223a-223h (collectively, "electrodes 223"). For example, balloon 211a is equipped with surface-mounted electrodes 223a and 223b, balloon 211b is equipped with surface-mounted electrodes 223c and 223d, and so on. In the embodiment of FIG. 7A, the surface-mounted electrodes 223 include metallic ring structures that can be fixedly mounted along an exterior circumferential surface of each balloon 211.

As depicted in FIG. 7B, the treatment tip 204 of the instrument 200 can include a series of inflatable dilation balloons 213a-213e (collectively, "balloons 213") having different sizes or shapes. For example, balloons 213 include a first set of balloons (e.g., balloon 213a and balloon 213c) having a largest size, a second set of balloons (e.g., balloon 213b and balloon 213d) having a medium size, and a balloon 213c having the smallest size. Balloons 213 can be arranged in a series and spaced apart by a separation distance to expose intermediate shaft portions 226). In some cases, each of the balloons 213 is equipped with multiple surface-mounted PFE electrodes of a set of surface-mounted PFE electrodes 227a-227j (collectively, "electrodes 227"). For example, balloon 213a is equipped with surface-mounted electrodes 227a and 227b, balloon 213b is equipped with surface-mounted electrodes 227c and 227d, and so on. As depicted in FIGS. 7A and 7B, a spacing of the balloons 211 and 213 by the separation distance 225 can provide increase bendability and maneuverability of the treatment tip 204 even when the balloons are inflated, thereby providing a treatment tip that can conforming to the shape of the anatomy (e.g., a tortuous curvature of sinus ostia).

Figures 8A, 8B:
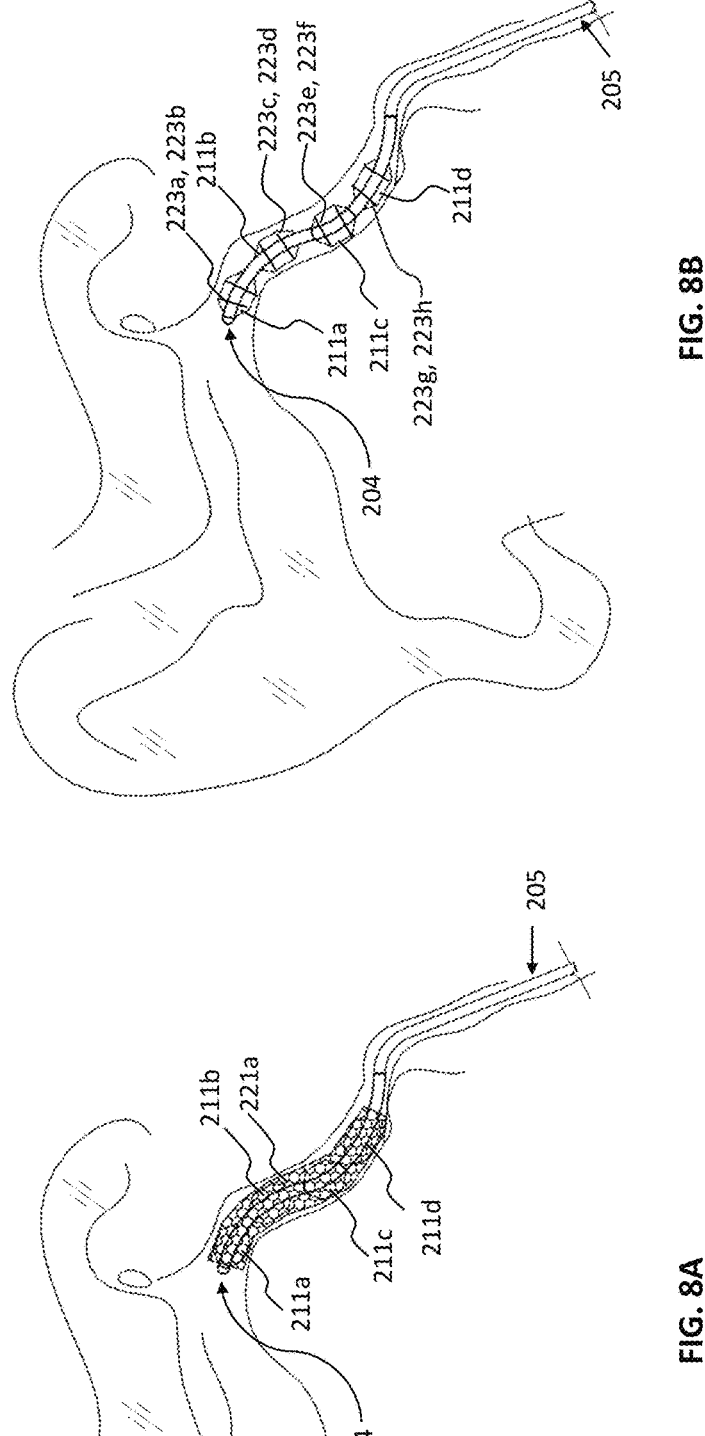
FIGS. 8A-8B show side views of the instrument of FIGS. 6A and 7A, respectively, within a Eustachian tube, in accordance with various embodiments.

For example, as depicted in the implementations shown in FIGS. 8A-8B, a Eustachian tube or other anatomical cavity in the ear, nose, and throat region can include a tortuous path in which the treatment tip 204 can be advantageously inserted to deliver dilation treatment, PFE treatment, or a combination thereof. In this example, the Eustachian tube has an S-shape path, and the treatment tip 204 of the instrument can be configured to dilate the path while reducing of a balloon sliding out of position during inflation due to the anatomical passage not being fully longitudinally straight or symmetric. In the example depicted in FIG. 8A, the treatment tip 204 can have a configuration including multiple balloons 211 and a mesh electrode 221a similar to the configuration depicted in FIG. 6A. In some cases, the series of balloons 211 can significantly reduce the likelihood of the treatment tip 204 sliding out of position during the balloon inflation process as compared with embodiments that use a single balloon. For example, due to small gaps in between each pair of consecutive balloons 211, the intermediate shaft portions can have increased flexibility that allow the tip 204 to conform to the curvature of the anatomical passage.

Similarly, in the example depicted in FIG. 8B, the treatment tip 204 can have a configuration with multiple balloons 211 and surface mounted electrodes 223 for each balloon 211, similar to the embodiment of FIG. 7A. Here again, the series of smaller balloons 211 can significantly reduce the likelihood of the treatment tip 204 sliding out of position during the balloon inflation process as compared with embodiments that use a single balloon. For example, the small gaps in between each balloon 211 increase a flexibility of the intermediate shaft portions between the balloons 211 for the tip 204 to conform to the curvature of the anatomical passage.

In some embodiments, the treatment tip 204 can include a configuration including balloons having varying sizes, similar to the embodiment of FIG. 7B. For example, the first balloon in the series of balloons 213 (e.g., balloon 213a) and the last balloon in the series of balloons 213 (e.g., balloon 213c) can be larger than other balloons of the series of balloons 213. This can cause the balloons 213a and 213e to serve as anchors when inflated, thereby stabilizing intermediate balloons 213b, 213c, and 213d while all of the balloons 213b, 213c, and 213d are inflated within the tortuous path to dilate the targeted tissue and delivery PFE treatment. In these above-described embodiments, a separation of consecutive balloons by the separation distance 225 can provide increased flexibility of the treatment tip 204 so that the treatment tip 204 can readily conform to complex shapes such as the S-shaped Eustachian tube, even when the balloons are fully inflated.

Accordingly, as depicted in the examples in FIGS. 1-8B, the PFE delivery instrument 200 of the system 10 can optionally be implemented in a manner that integrates PFE electrodes with dilation balloons to increase tissue treatment options using a single instrument (during a single surgical intervention) while also increasing the likelihood improved surgical outcomes. For example, various embodiments described herein can contemporaneously achieve mechanical dilation of an obstructed passage while also delivering PFE from PFE electrodes engaged with the targeted tissue to induce apoptosis in the abnormal cells/diseased tissue, which can advantageously induce healthy regeneration and proliferation of new cells. Optionally, some versions of the PFE electrodes (described above) can comprise a self-expanding stent structure that can engage against the targeted tissue to deliver PFE without balloon dilation of the tissue, which can be useful in some spaces of a Eustachian tube, paranasal sinuses, intra-sinuses, and others. This optional approach can be desired for procedures that do not require significant expansion and/or remodeling of the tissue passage using mechanical dilation of the passage prior to outputting PFE.

In light of the teaching herein and examples described in connection with FIGS. 1-8B, a variety of balloon configurations and PFE electrode structures can be implemented in PFE delivery instrument 200. Additionally, based upon the teaching herein, any feature of the embodiments depicted in FIGS. 4-8B can be used in combination with additional features of other embodiments depicted in FIGS. 4-8B. Further, based upon the teaching herein, the PFE electrodes can include a variety of shapes and structural configurations, including those that from partially cover the balloon, to those that fully cover the balloon, and to those that are implemented along the PFE delivery instrument 200 without any dilation balloon.

Additionally, in light of the teaching herein and examples in connections with FIGS. 1-8B, it should be that the PFE generator 130 of the control console 100 (FIG. 1) can be configured to output a variety of PFE waveforms from the PFE electrode structures described above. In particular embodiments described herein, the PFE output by the generator 130 and delivered from the instrument 200 provides an electric field that is applied to the targeted tissue in a series of rapid bursts to cause electroporation at the targeted tissue, thereby inducing cell membrane destabilization to induce apoptosis without thermal ablative effects (e.g., necrosis of the tissue). Optionally, the PFE output by the generator 130 and delivered from the instrument 200 can provide highly effective treatment at the targeted tissue within an ear, nose, or throat while achieving improved convenience for both the clinician and the patient—for example, while the patient is awake (e.g., avoiding general anesthesia) and using only a local topical anesthetic (e.g., temporary effectives and rapid recovery). In one example, the PFE generator 130 may be configured to output a PFE (delivered from the treatment tip 204 of the instrument 200) in the form of an electric field with a PFE waveform having a voltage amplitude of greater than 800 volts and a pulse width no greater than 5 microseconds (e.g., preferably a pulse width of 50 nanoseconds to 3 microseconds), which can result in sufficient PFE that induces induce apoptosis of the cells of the treated tissue while avoiding thermal ablative effects (e.g., avoiding necrosis). Additional options for the characteristics of the PFE waveform useful in particular embodiments described herein are described in more detail below.

Figure 9:
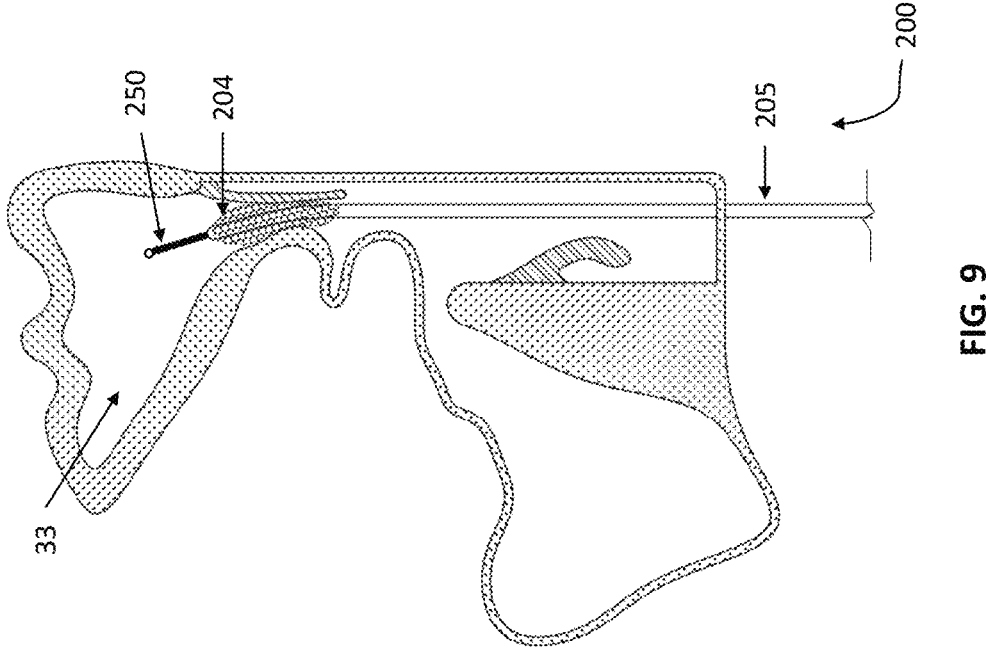
FIG. 9 shows a side view of a distal portion of an optional instrument for the system of FIG. 1, within a frontal sinus ostium, in accordance with various embodiments.

Referring now to FIG. 9, some embodiments of the system 10 include using the PFE delivery instrument 200 in combination with an illumination element, medical imaging, or both. For example, certain types of anatomies, such as frontal sinus 33 of the patient 30, can be complex to access, and the instrument 200 can include a transdermal illumination LED 250 positioned along the treatment tip 204 (e.g., at the most distal end of the treatment tip 204) for a user to confirm access to the targeted anatomical cavity by illuminating light at the tip 204 sufficient to view trans-dermally through the skin (viewable by the eyes of the physician). Optionally, the LED 250 may be replaced or combined by an electromagnetic marker or sensor which may also be used to confirm anatomical location with high accuracy relative to a CT or MRI image. As previously described in connection with FIGS. 1-8B, the treatment tip 204 may include at least one dilation balloon (e.g., any one or combination of balloons 210, 211, 213), at least one PFE electrode (e.g., any one or combination of electrodes 220, 221, 222, 223, 227), or a combination of both. This can treat ostia of paranasal sinuses by opening a blocked passage via dilation, by shrinking the inflammation of ostia tissue using PFE, or by performing dilation and delivering PFE.

Referring now to FIGS. 9-11B, some embodiments of the system 10 include the PFE delivery instrument 200 with an adjustable PFE electrode that is adjustable to conform to the shape of an anatomical cavity, optionally, without the use of an expandable balloon. For example, the PFE delivery instrument 200 can be used in anatomical spaces such as sinus cavities 33 having an accumulation of diseased cells resulting in mucosa thickening, sinus infection, or other related disease. In this embodiment, the treatment tip 204 of the instrument 200 includes a user-controlled, expandable mesh PFE electrode 231 that can be actuated (e.g., via one or more control wires extending to a dial or other actuator along the handle 260 (FIG. 3)) to continuously expand and conform to the cavity volume 33 as shown in FIGS. 10A-10B. After the expandable mesh PFE electrode 231 is used to deliver the PFE treatment (e.g., via activation of the button 270 (FIG. 3), the user can collapse the mesh PFE electrode 231 (e.g., using the one or more control wires) for purposes of withdrawing the treatment tip 204 out of the cavity 33. Alternatively, the PFE electrode 231 may be expanded using a compliant balloon positioned within the mesh structure of the electrode 231, which when inflated will flexibly expand and conform to the shape of the cavity being treated. Additionally, in other implementations beyond the sinus cavity example depicted in FIGS. 10A-

Figure 11B:
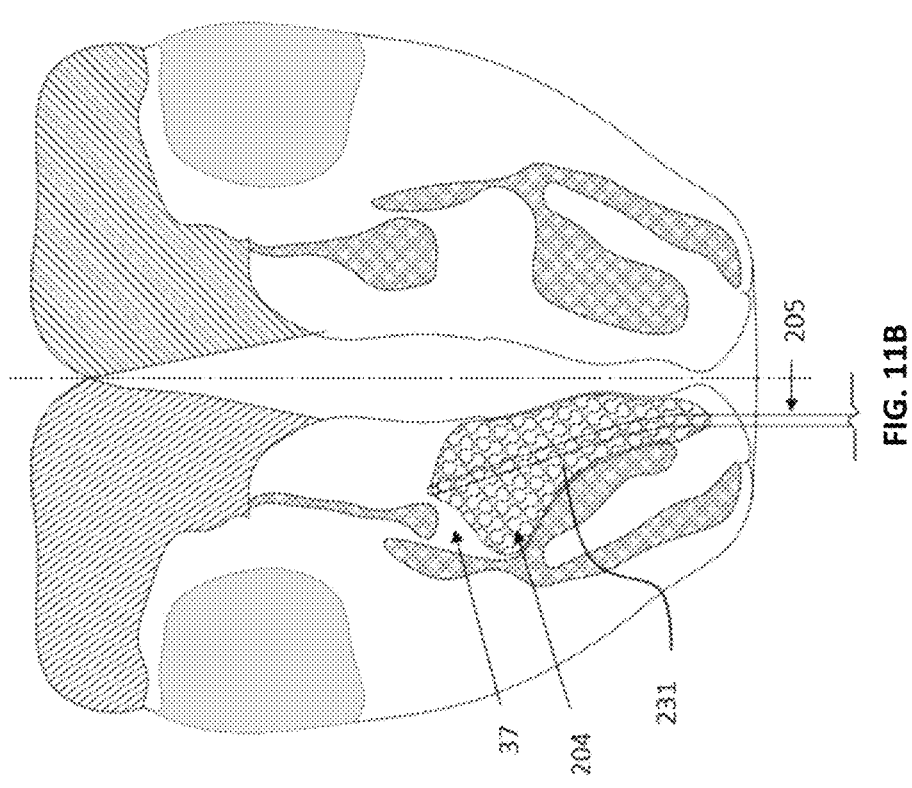
FIGS. 11A-11B show side views of a distal portion of an optional instrument for the system of FIG. 1, in its non-expanded (FIG. 11A) state and its expanded (FIG. 11B) inside a nasal cavity, in accordance with various embodiments.
Figure 11A:
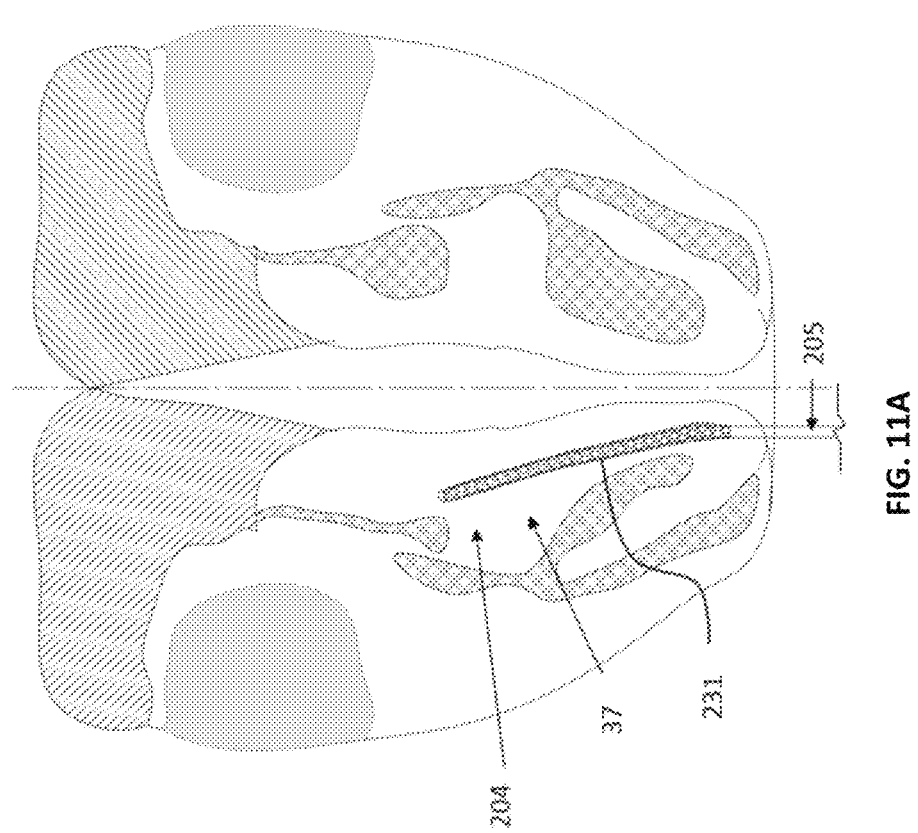

10B, the PFE delivery instrument may be delivered to, and then the PFE electrode 231 expanded using a compliant balloon within, other anatomical structures such as nasal passage 37 as shown in FIGS. 11A-11B.

Figure 10B:
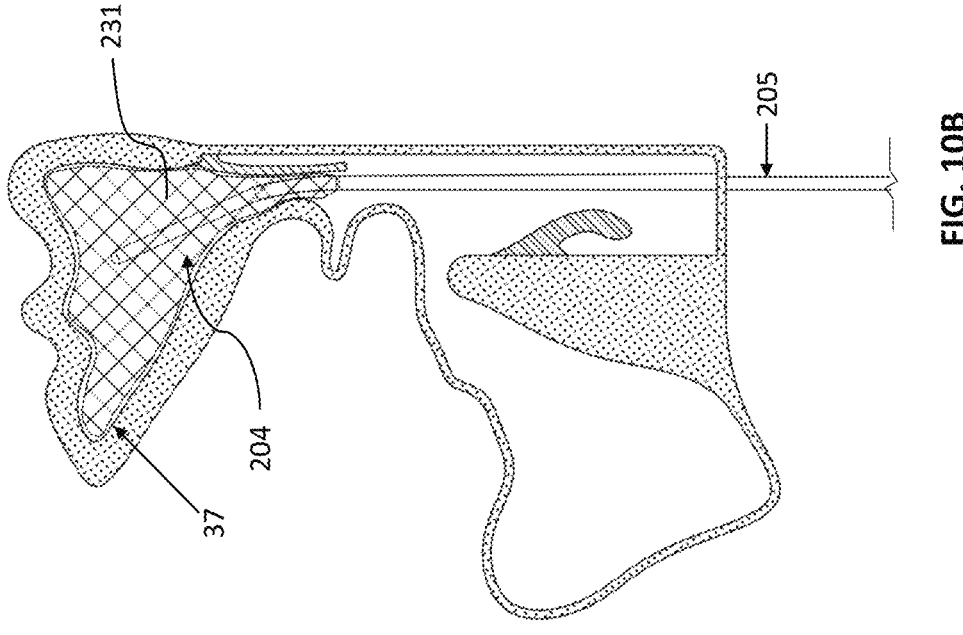
FIGS. 10A-10B show side views of a distal portion of an optional instrument for the system of FIG. 1, in its non-expanded state (FIG. 10A) and its expanded state (FIG. 10B) within a sinus cavity, in accordance with various embodiments.
Figure 10A:
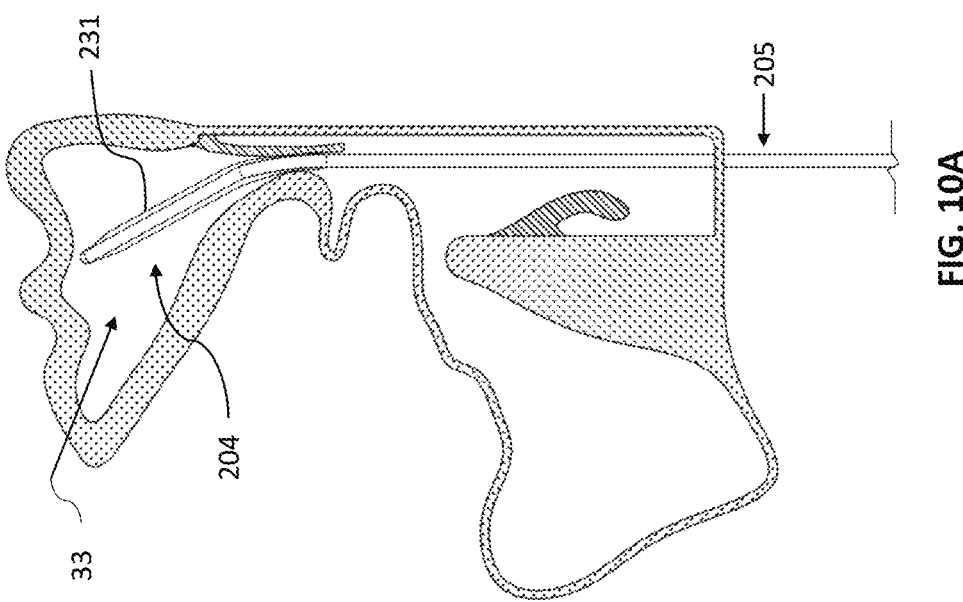

The use of PFE within the sinus cavity, FIGS. 9 and 10A-B, may treat chronic infection and biofilm by killing the diseased tissue and/or antigens causing the biofilm, chronic infection, and/or mucosa thickening via apoptosis, and at the same time stimulate the tissue where the PFE is delivered to regenerate with healthy tissue. This is achieved due to the apoptosis process triggering the T-cells, and other infectious fighting cells to come at the area where the PFE is delivered, where the dead apoptotic cells are removed by the T-cells and at the same time the tissue is regenerated with healthy non-infectious tissue.

Biofilm bacteria are shielded from environmental stresses such as antimicrobial agents, by the protective matrix of extracellular polymeric substances (EPS), making biofilms significantly more difficult to eradicate. Biofilms can form on a variety of tissues, including paranasal sinuses and sinus cavities. The bacteria within biofilms often exhibit unique behaviors and interactions, including enhanced nutrient exchange and genetic exchange, which contribute to their resilience and adaptability. Biofilms play significant roles in both beneficial processes, such as bioremediation, and harmful contexts, such as chronic infections. PFE may be applied in cases where the biofilm bacteria are causing chronic infection to break out the biofilm and the living bacteria within the EPS layer. For example, within the sinuses the PFE may be activated, as shown in FIGS. 9 and 10A-B, to kill excessive bacteria in the biofilm since the PFE may penetrate the EPS layer shielding the bacteria. Further, the PFE may be used to disrupt the biofilm matrix thus significantly reducing bacteria resistance to drugs and antibiotics which may be used in conjunction with PFE or taken at a later time to eradicate bacteria.

Figure 12:
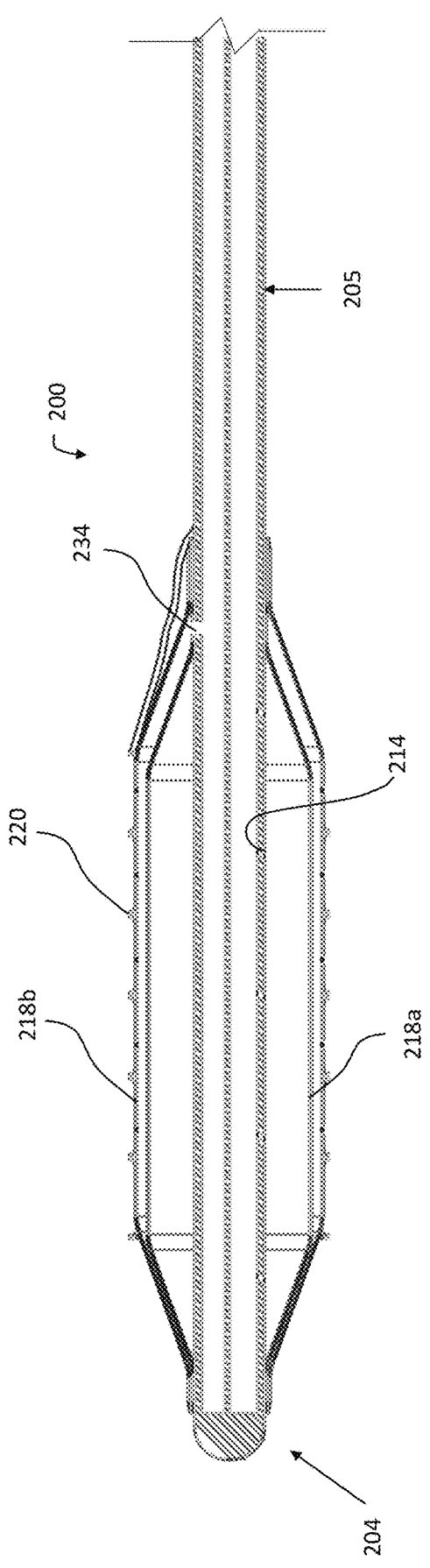
FIG. 12 shows a side view of a two-layer balloon configuration at a distal portion of an optional instrument for the system of FIG. 1, in accordance with some embodiments.
Figure 13:
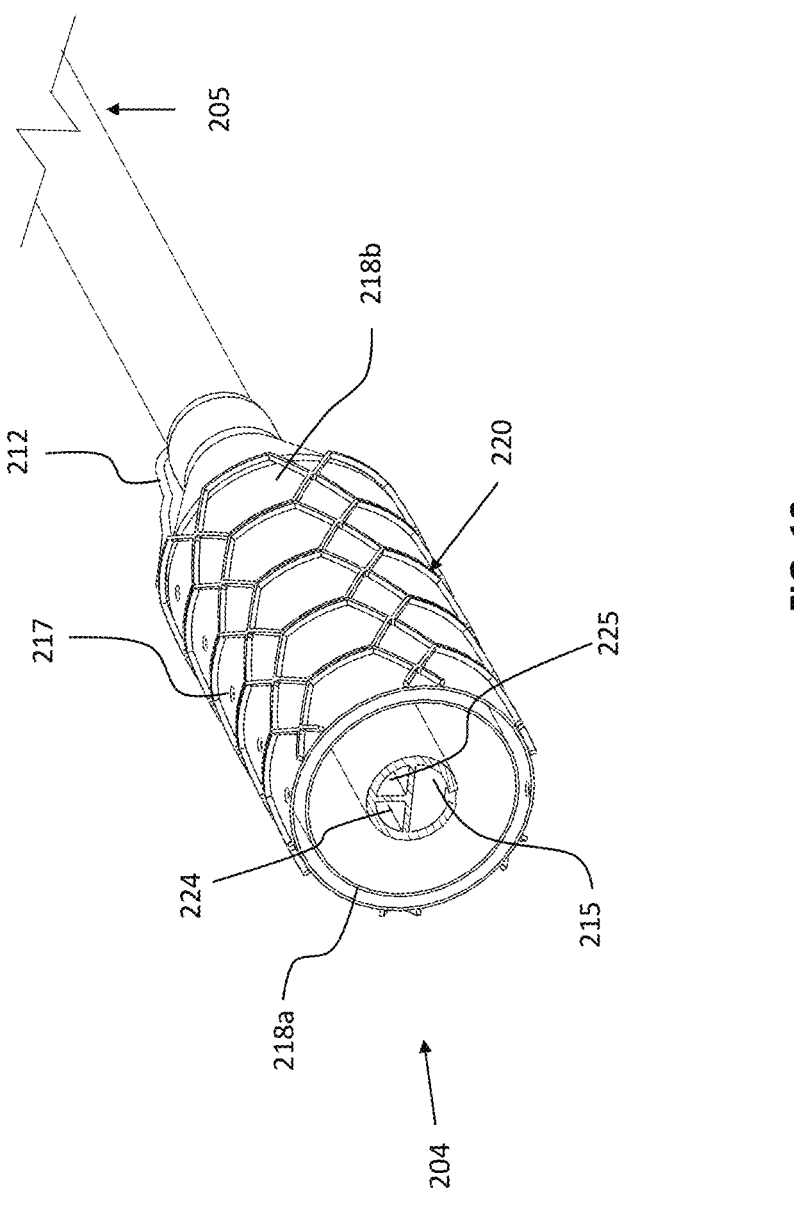
FIG. 13 shows a cross-sectional perspective view of a distal portion of an optional instrument for the system of FIG. 1, which includes a drug delivery option, in accordance with some embodiments.

Referring now to FIGS. 12-13, some embodiments of the system 10 include the PFE delivery instrument 200 in which the treatment tip 204 is configured to contemporaneously deliver a drug or other therapeutic agent and deliver the PFE treatment at the targeted tissue. For example, the control console 100 (FIG. 1) can be configured to output PFE from the treatment tip 204 to open the pores of cells for reversible electroporation (in which the cells absorb a drug or other therapeutic agents much faster as compared to not being exposed to the PFE) while the treatment tip 204 also outputs fluid delivery of drug or another therapeutic agent. In the embodiment depicted in FIG. 12, the treatment tip 204 includes two balloon structures—an inner balloon 218a which operates in a similar manner as the balloon 210 of FIGS. 3-5D to expand in size and compress a mesh PFE electrode against the targeted tissue, and an outer balloon 218b which includes outer pores 217 for delivering a fluid drug or agent outwardly to the targeted tissue. The pores 217 of the outer balloon 218b can express a fluid such that, when the drug or agent is delivered between the inner balloon 218a and the outer balloon 218b, the pores 217 through the exterior circumferential surface of the outer balloon 218b express the fluid drug or agent outwardly toward the targeted tissue that the mesh PFE electrode 220 is also contacting. The electrode 220 can output PFE prior to, during, or after the pores 217 output the drug or agent to the tissue. In this embodiment, the elongated shaft 205 is equipped with multiple lumens, including the inflation lumen 215 (to deliver the inflation fluid into the inner balloon 218a), and a first fluid delivery lumen 224 (in fluid communication with the outer balloon 218b via one or more ports 234 so that a first drug or agent can be delivered from the pores 217 of the outer balloon 218*b*), and a second fluid delivery lumen 225 (in fluid communication with the outer balloon 218*b* via one or more ports (e.g., like port 234) so that a second drug or agent can be delivered from the pores 217 of the outer balloon 218*b*). As such, the first and second fluid delivery lumens 224 and 225 may be used to deliver different types of drugs through the outer balloon 218*b*, and the inflation lumen 215 is isolated and in communication with the inner balloon 218*a* to inflate the inner balloon 218*a*.

Figure 14:
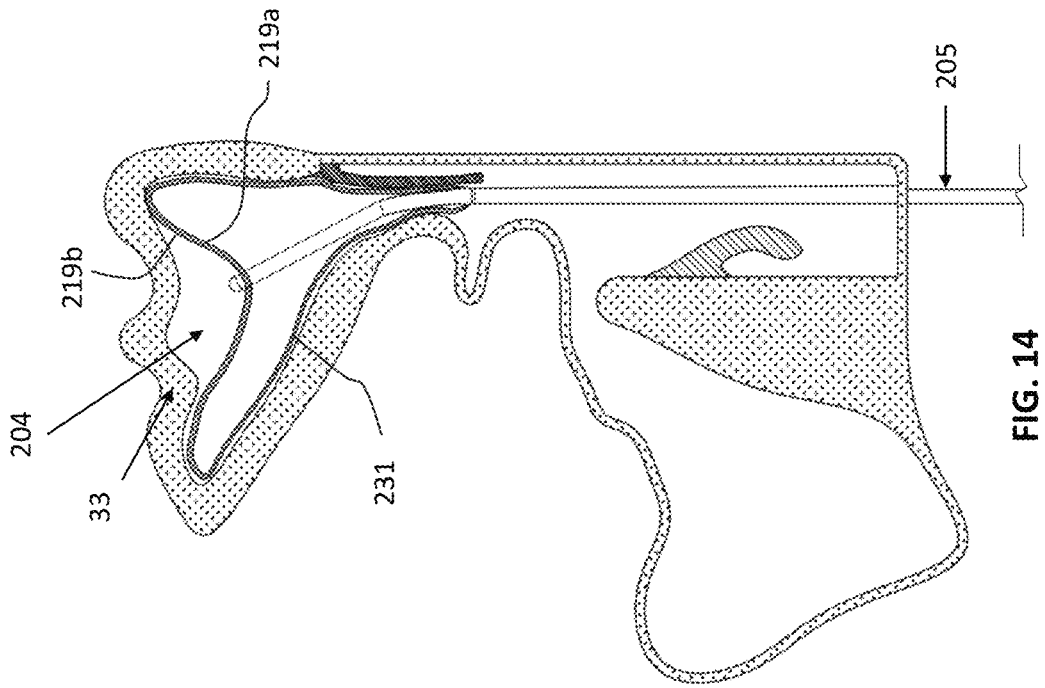
FIG. 14 shows a side view of a two-layer compliant balloon configuration at a distal portion of an optional instrument for the system of FIG. 1, which is conformed to an anatomy shape, in accordance with some embodiments.

Referring to FIG. 14, additional embodiments of the system 10 can contemporaneously deliver a drug or other therapeutic agent and deliver the PFE treatment at the targeted tissue. Here again (similar to the previous example depicted in FIGS. 12-13), the control console 100 can be configured to output PFE from the treatment tip 204 to open the pores of cells for reversible electroporation (in which the cells absorb a drug or other therapeutic agents much faster as compared to not being exposed to the PFE) while the treatment tip 204 also outputs fluid delivery of a drug or other therapeutic agent. In the embodiment depicted in FIG. 14, the balloons can be compliant balloons that expand in a flexible manner to conform to the shape of the anatomical cavity along with the conformable mesh PFE electrode 231 (e.g., refer also to FIGS. 10A-10B and FIGS. 11A-11B). For example, the treatment tip 204 can include an inner compliant balloon 219*a* which operates to expand in size and compress the mesh PFE electrode 231 against the targeted tissue. The treatment tip 204 can also include an outer compliant balloon 219*b* which includes outer pores (e.g., similar to pores 217 illustrated by FIG. 13) to deliver the fluid drug or agent outwardly to the targeted tissue. The expandable mesh PFE electrode 231 can be located outside of the outer compliant balloon 219*b*. When the inner balloon 219*a* is inflated, the PFE electrode 231 can conform to the cavity 33 being treated, achieving at least partial contact with the tissue surface in the cavity 33. Also, during or after the expansion of the PFE electrode 231, the fluid drug or agent can be delivered between the inner balloon 219*a* and the outer balloon 219*b* (e.g., similar to the operation of the treatment tip 204 depicted in FIGS. 12-13 including ports 234 and pores 217) such that the fluid drug or agent is output through pores in the exterior circumferential surface of the outer balloon 219*b* toward the targeted tissue that the mesh PFE electrode 231 stimulates.

Figure 15B:
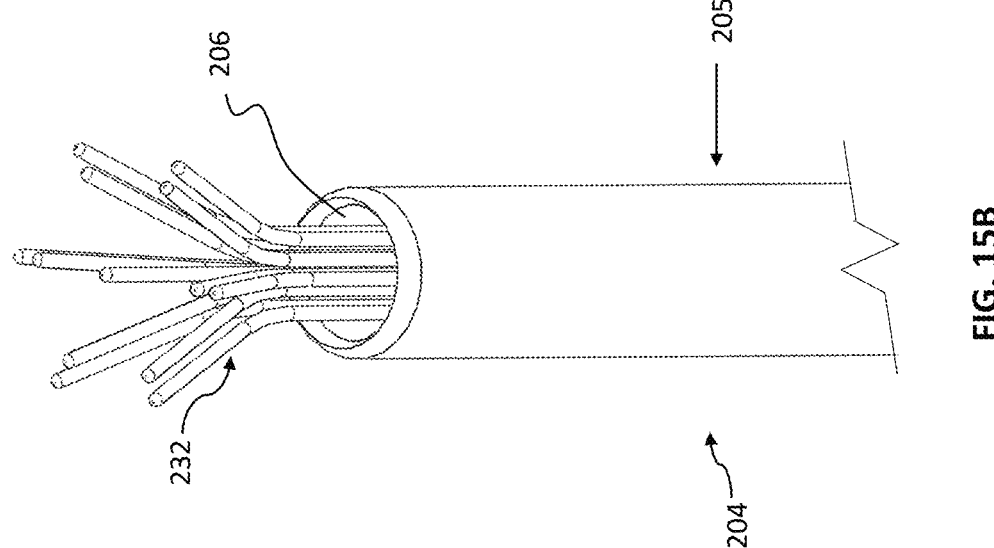
FIGS. 15A-15B show perspective views of a focal point instrument which can be included with, or operate as, the instrument of the system of FIG. 1, in accordance with some embodiments.
Figure 15A:
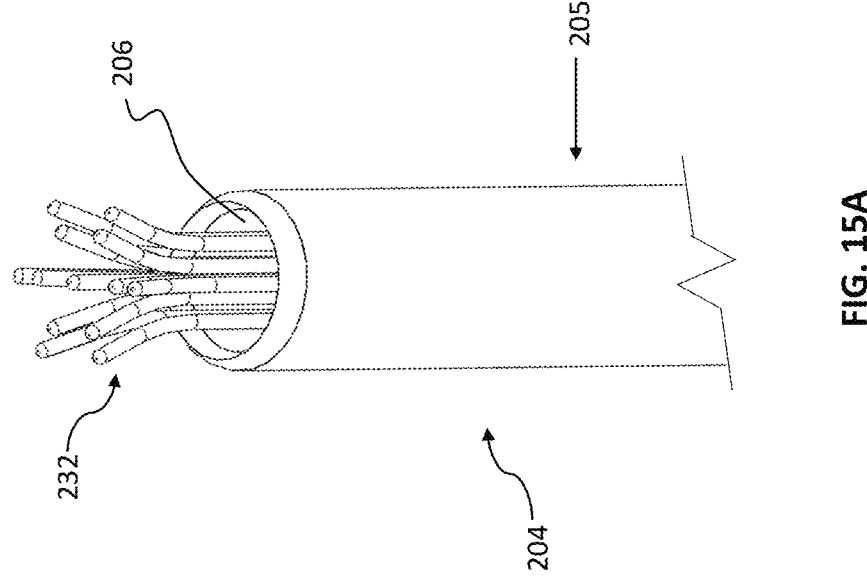
Figures 16A, 16B:
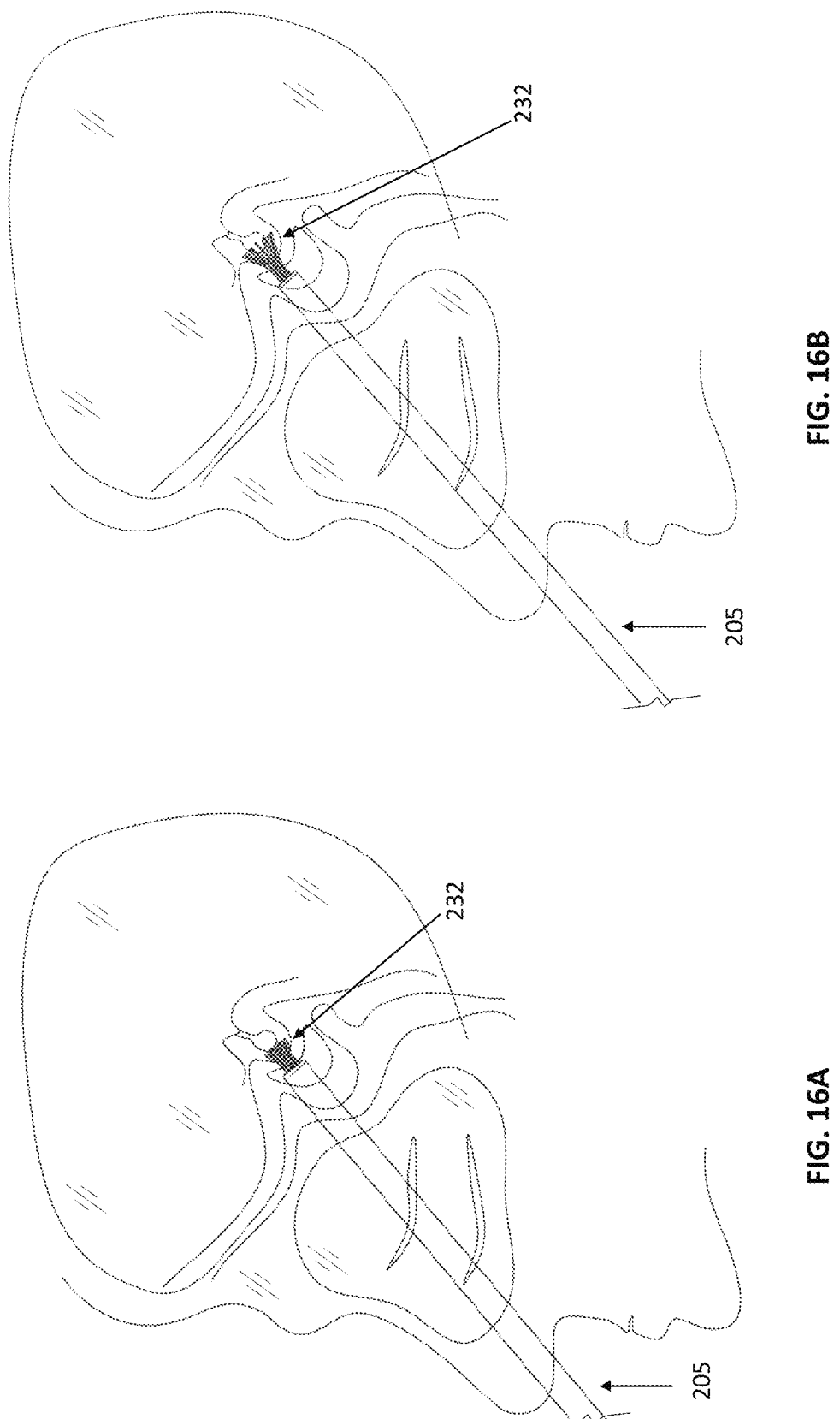
FIGS. 16A-16B show side views of the focal point instrument of FIGS. 15A-15B, within cranial tissue, in accordance with some embodiments.

Referring now to FIGS. 15A-16B, some embodiments of the system 10 include the PFE delivery instrument 200 in which the treatment tip 204 includes movable needle PFE electrodes 232 configured to output PFE over a small, predefined area on the surface of a targeted tissue area. In the embodiment depicted in FIGS. 15A-15B, treatment tip 204 includes a plurality of needle electrodes 232 that are slidable relative to the elongated shaft 205, which includes a distal opening 206 in this embodiment. Each of the needle electrodes 232 can include a needle shaft body that extends distally to a curved region, which then extends distally to an electrode needle tip. As depicted in FIGS. 15A and 16A, needle PFE electrodes 232 can be advanced to a first extension distance distal to the distal opening 206 such that the PFE output from the needle PFE electrodes 232 is delivered over a targeted small area primarily along a surface of the tissue (e.g., the pituitary gland or other intracranial tissue as depicted in FIG. 16A). As illustrated in FIGS. 15B and 16B, the needle PFE electrodes 232 can be advanced to a second, greater extension distance distal of the distal opening 206 such that the PFE output from the needle PFE electrodes 232 is delivered submucosally in a depth of the targeted small area (again, such as in a depth of the pituitary gland or other intracranial tissue as shown in FIG. 16B). In such intracranial procedures, especially when the diseased cells are located submucosally, needle PFE electrodes 232 of the treatment tip 204 as depicted in FIG. 16B can be advantageously advanced to a submucosal depth so the PFE is delivered in proximity to the diseased tissue.

Figure 17:
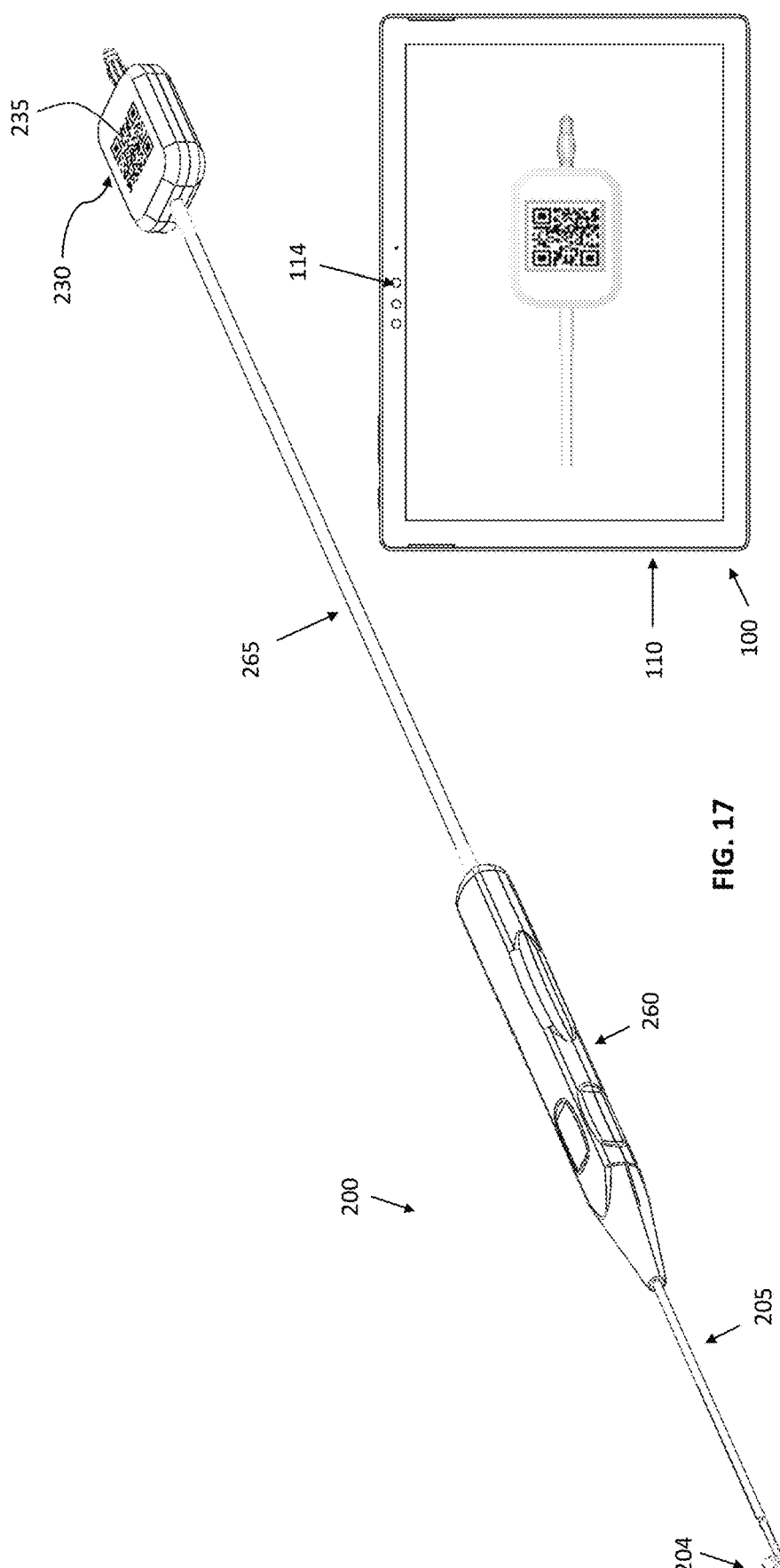
FIG. 17 shows a perspective view of the instrument of the system of FIG. 1 along with an optional device connector and image capture device, in accordance with some embodiments.

Referring now to FIG. 17, in some embodiments, the instrument 200 can be equipped with an identifier (such as a QR code 235) that is readable by the control console 100 (FIG. 1) to thereby impact the operation of the system 10. For example, when the control console captures the QR code 235 of the particular instrument 200 that releasably mated with the PFE generator 130 of the control console 100, the control console may recognize the type of instrument 200 and then, in response thereto, enable the generation of PFE output (because the instrument 200 is an authorized instrument), modify the characteristics of the PFE output (e.g., to induce IRE or RE, to treat a surface tissue or a submucosal tissue, etc.), to communicate (e.g., via a wired or wireless connection to the internet) with the cloud server system 50 to transmit treatment data from the control console 100 to the cloud server 50 indicative of the use of that particular instrument 200 (having the identifier 235) with the particular patient 30 on that date, or a combination thereof. Additionally, responsive to the control console 100 capturing the QR code or other identifier 235 of the instrument, the control console 100 may communicate (e.g., via a wired or wireless connection to the internet) with the cloud server system 50 to validate that particular instrument 200 is authorized for use. As shown in FIG. 17, the identifier in this embodiment is a QR code 235 affixed to the instrument connector 230 of the selected instrument 200 (e.g., at a proximal end of a cable 265 while the handle 260 is at the distal end of the same cable 265), which is shaped to mate with the generator 130 of the control console 100 (FIG. 1). In this embodiment, each QR code 235 is unique for its particularly associated instrument 200 and may only be authorized for use once (e.g., via a verification at the cloud server 50), thereby ensuring sanitary disposal of each instrument 200 after its initial use and further confirming the PFE signal is output to authorized equipment for consistent safety. In this example, the QR code 235 affixed to the instrument connector 230 is captured by a camera 114 of the user interface 110 of the control console 100 (FIG. 1). For example, the user interface 110 can include a tablet device having a touch screen and a camera mounted adjacent to the touchscreen display. In use, the user interface can be prompted to activate the camera for use of the control console with a new instrument 200, and the onscreen prompts would alert the user to scan the QR code using the camera 114. The tablet device can be movably relative to the generator 130 of the control console 100 such that the camera 114 can be directed toward the QR code 235 on the connector 230 after it is plugged into the generator 130 (FIG. 1), or the QR code 235 on the connector 230 can be positioned in front of the camera 114 of the user interface 110 immediately before the connector 230 is plugged in the generator 130. In response to the QR code 235 being captured and then authorized for use with 41 the PFE generator 130 (via the connection with the cloud server 50), the QR code 235 can also be assigned to the patient 30 (FIG. 1) or otherwise recorded to the patient's Electronic Health Record (EHR) file associated with the medical procedure, thus allowing the patient to monitor the procedure efficacy over time. The QR code 235 may also be used to automate reporting of complaints or defects (e.g., using the user interface 110 of the control console 100 in communication with the cloud server 50 to report such a problem with a particular instrument 200), or to prevent product usage for a certain output type (e.g., preventing a PFE output to induce IRE when the instrument 200 includes a fluid drug delivery lumen (FIGS. 12-13) for use with a different PFE output that induces RE during the drug delivery).

Referring now to FIG. 18, some implementations of a process 1800 for using the unique identifier (e.g. a QR code 235) of a PFE delivery instrument 200 can include the operation 1810 for generating a unique code for each instrument. For example, the QR code can generated for the instrument at the manufacturing facility where the instrument 200 is also manufactured. At the time when the QR code is generated, a computer system at the manufacturing facility adds the QR code to a database stored at the external cloud server 50 (FIG. 1). In operation 1820, when the user starts the procedure, the QR code affixed on the instrument is scanned using the camera of the control console (e.g., refer to FIGS. 1 and 17). In response to scanning the QR code at the control console, the control console queries the cloud server 50 (FIG. 1), which compares the scanned QR code to the database to confirm if the instrument is authorized for use (e.g., a new instrument). If the QR code indicates that the instrument is authorized, the control console receives an indication of such authorization and initiates the PFE generator to prepare for the output of PFE treatment with the properly connected instrument. Alternatively, if the QR code indicates that the instrument was previously used or otherwise not authorized, the control console receives an indication of such unauthorized instrument and disables (or maintains a disabled state for) the PFE generator. In operation 1830, after confirming the authorization to use the instrument 200 having the QR code, the data generated during the procedure, such medical images of anatomical locations where PFE was delivered during use, is stored locally on the controller console (and optionally, uploaded to the cloud server 50) and linked to the QR code that was initially scanned in operation 1820. Optionally, when the QR code is scanned, the controller console automatically stores the instrument identification and where the instrument is being used (e.g., with a designated location of the control console). Thus, in operation 1840, if an error occurs during the procedure, the controller console automatically transmits the information related to the error to the cloud server 50. Also, in operation 1850, the QR code scanned in operation 1820 may also be associated with the particular patient with which the instrument is used. For example, during the procedure, the data such as endoscopic images, and others, are stored in a folder named same as the QR code. After the procedure, the QR code may be provided to the patient, stored in the Electronic Health Record (EHR) of the patient, or both. When the doctor, or patient, subsequently scans the QR code using a smartphone, tablet, or the control console, a hyperlink is presented to provide access the data generated during the procedure.

Figure 19B:
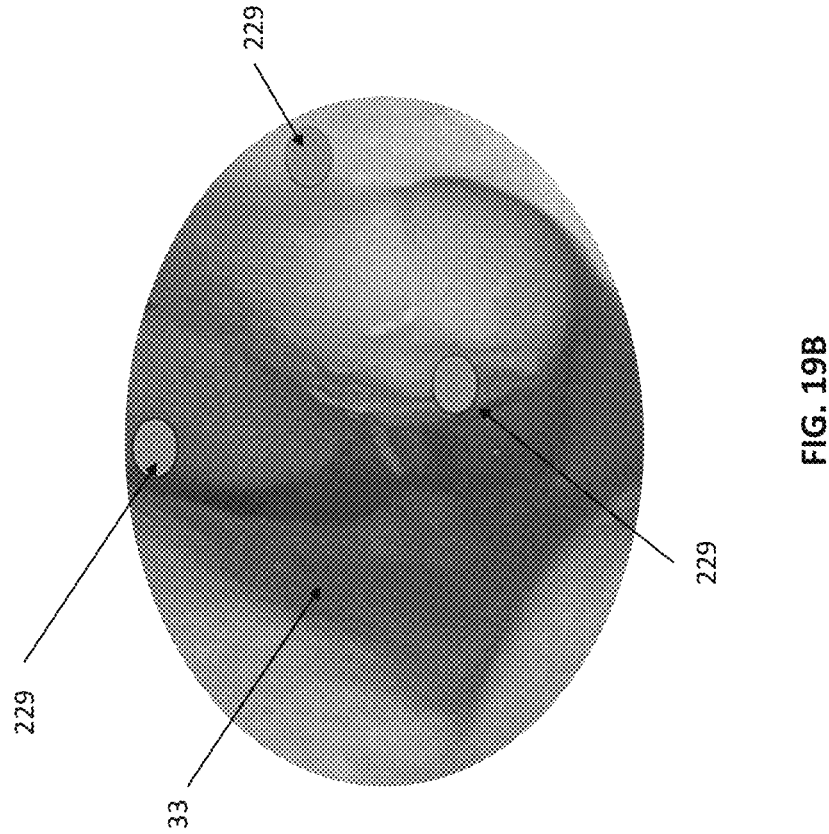
FIGS. 19A-19B show medical images of the instrument of the system of FIG. 1 used in accordance with optional implementations of a treatment tracking algorithm.
Figure 19A:
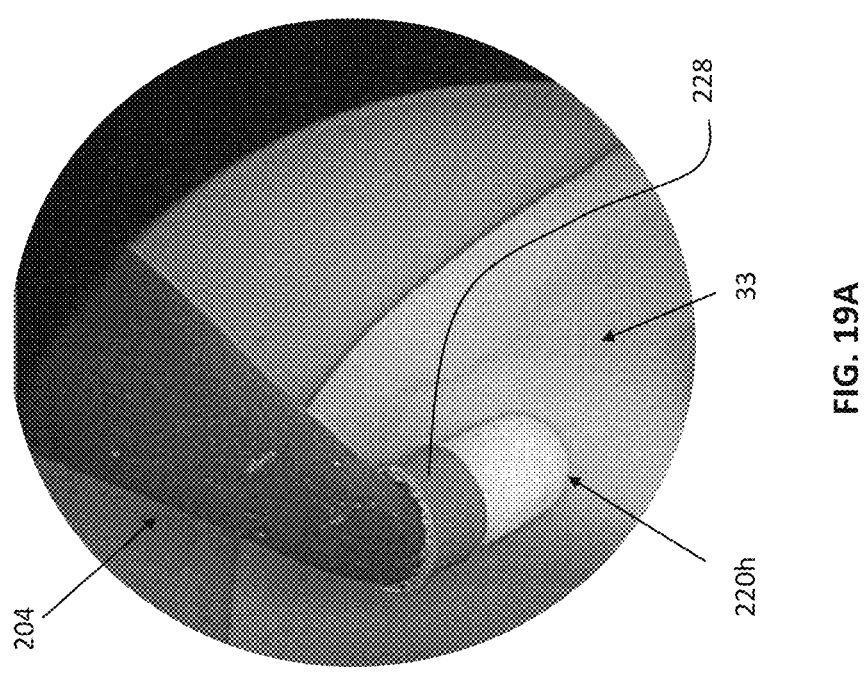

Referring now to FIGS. 19A-19B, as previously described in some embodiments, the instrument 200 can be used in conjunction with an endoscope 45 (FIG. 1) to provide medical imaging of the treatment tip 204 within the patient during PFE delivery at the targeted tissue. In many circumstances, the PFE output from the treatment tip 204 may not result in visible marking or discoloration upon the treated tissue, yet the system described in this embodiment can optionally provide the ability to visually record and track the anatomical location of previously treated tissues for each particular patient. In this embodiment depicted in FIGS. 19A-19B, the treatment tip 204 of the instrument 200 can include a dome-shaped PFE electrode 220h (although any of the other electrodes 220 and 220a-g may also be implemented here) and a marker band 228 positioned adjacent to the electrode 220h. The endoscope 45 (FIG. 1) is advanced adjacent to the treatment tip 204 so as to provide video data of the use of the treatment tip 204 in an anatomical cavity (e.g., the nasal cavity 33 in this example). The control console 100 (FIG. 1) is configured to receive the video data from the endoscopy system 40 and to generate (and then store) one or more new medical images that superimpose treatment site markings 229 (FIG. 19B) over the original medical image recorded by the endoscope at the specific locations where the PFE was output from the electrode 220h. In this embodiment, location of the band 228 (or, optionally, the electrode itself 220h) is continuously tracked in the endoscopic video data by a machine learning algorithm, which upon activation of the PFE output from the electrode 220h, then identifies the location within the endoscopic image where the PFE was delivered to the tissue and stores such new image(s) in the memory of the control console 100. As shown in FIG. 19B, the markings 229 depict historical treatment areas where PFE was delivered within a nasal cavity 33. The markings can be color coded, for example, with different colors may be used to show different amounts of PFE delivered.

Referring now to FIG. 20, some implementations of a process 2000 for tracking the location of the treatment tip and generating markings of the treatment locations (e.g. as shown in FIGS. 19A-19B) can include the operation 2010 of recording an endoscopic view of a PFE delivery instrument having a band or other unique feature that is visibly detectable within the endoscopic image. For example, the treatment tip 204 can include a physical feature that is detectable by an AI image recognition software executed by the control console (which receives the endoscopic video data in real time from the endoscopy system 40 (FIG. 1)). In operation 2020, in response to the user activating the PFE electrode to output the PFE treatment at an adjacent tissue site, an image of the endoscopic view is captured and stored on the control console. In operation 2030, the captured endoscopic image is modified to include one or more markings at the AI-detected location(s) of electrode (refer to electrode 220h in FIG. 19A and markings 229 in FIG. 19B) at the time of PFE activation. The markings may be added to the endoscopic image of the anatomic cavity while the treatment tip resides in that cavity too, or the markings can be added to an endoscopic image of the anatomic cavity that was recorded without the treatment tip being present in the field of view (e.g., recorded before or after the treatment tip was inserted). In operation 2040, the modified medical image (including the markings) and other procedure data may be transmitted from the control console to the cloud server 50 (FIG. 1), and optionally, can be presented at the user interface 110 of the control console 100 analysis by user at the clinical site.

Figure 21:
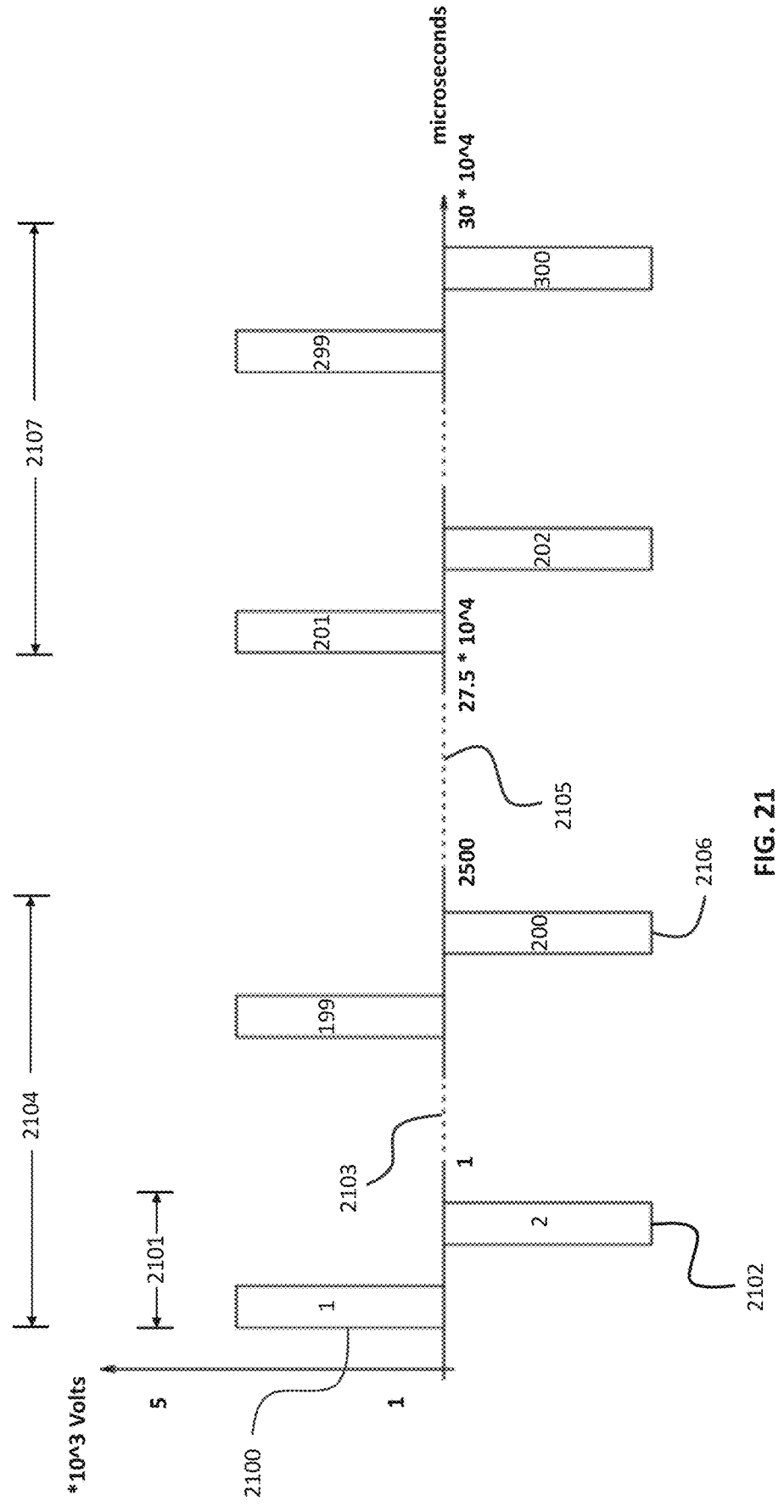
FIGS. 21-22 show examples of PFE waveforms output by the system of the FIG. 1, in accordance with some embodiments.
Figure 22:
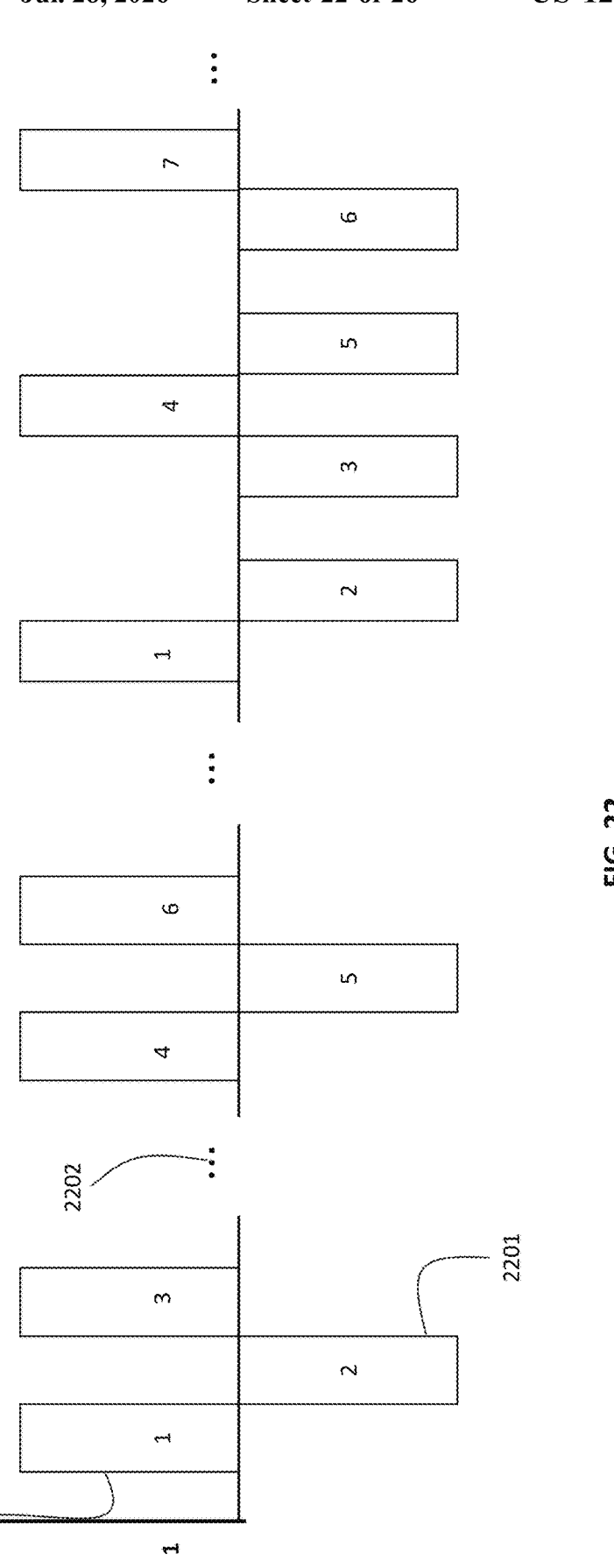

Referring now to FIGS. 21-22, some embodiments of the PFE generator 130 of the control console 100 (FIG. 1) can be configured to PFE in the form of PFE waveforms for induce apoptosis of the cells of the treated tissue. In this embodiment, and as previously described, the PFE output by the generator 130 and delivered from the instrument 200 provides an electric field that is applied to the targeted tissue in rapid bursts to cause electroporation, thereby inducing cell membrane destabilization to cause apoptosis and, preferably, while avoiding the thermal ablation energy (e.g., from RF, CA, or laser ablation) that induces the above-described necrosis of the tissue. For example, as shown in FIG. 21, the generator may be configured to output a PFE waveform with an amplitude 2100 of greater than 800V (preferably between 800V and 5 kV in this example) and pulse width 2106 of less than 5 microseconds (preferably about 50 nanoseconds to 3 microseconds in this example) such that there is a sufficient electric field resulting in PFE treatment without thermal ablative effects at the tissue site. As shown in FIG. 21, each burst 2104, 2017 can include a set of predefined pulses, and each set of pulses can include from 1 to 1,000 pulses in this example (the pulses are numbered in the diagram of FIG. 21). A pattern of pulses 2101 within each burst 2104, 2107 may be separated by a pulse delay 2103 (which can be between 1 microsecond and 1000 microseconds in this example) in such a way that the delivery of PFE can also, in addition to inducing the above-described apoptosis, stimulate the nerves located in proximity to the PFE electrode. Further, the intensity of neurostimulation may be increased by delivering a series of multiple bursts (e.g., refer to 2104 and 2107 in FIG. 21), and the consecutive bursts can be separated by a burst delay 2105 of at least than 50 milliseconds. In such circumstances, the time of the burst delay 2105 between the first burst 2104 and a subsequent burst 2107 can be long enough to allow for completion of the nerve stimulation during the first burst 2104 prior to outputting the subsequent burst 2107. Within each burst 2104, 2107, the frequency of pulses can be set to a value of about 400 kHz to about 10 MHz (which can be accomplished by the generator 130 (FIG. 1) by adjusting the value for the pulse delay 2103 between each pulse). Also, for each series of bursts (refer to the first burst 2104 and the subsequent burst 2107), the frequency of bursts can be set to a value of about 1 Hz to about 400 kHz (which can be accomplished by the generator 130 (FIG. 1) by adjusting the value for the burst delay 2105). As shown in FIGS. 21-22, a pulse can have a positive polarity, a negative polarity, or both (refer to FIG. 22 for a positive polarity 2200 and a negative polarity 2201). As shown in FIG. 22, the amplitude combination of positive 2200 and negative 2201 polarities may be delayed 2202 or may be continuous without a delay from the transition of one amplitude polarity to the next polarity. Thus, as shown in the examples in FIG. 22, the PFE output from the PFE generator can include a PFE waveform having a repeated pattern to provide an overall biased energy of positive polarity (without causing muscle contraction), the repeated pattern including a positive pulse, a negative pulse, and another positive pulse (refer to the left and middle of FIG. 22). Alternatively, or additionally, the PFE output from the PFE generator can include a PFE waveform having a repeated pattern to provide an overall biased energy of negative polarity (without causing muscle contraction), the repeated pattern including a negative pulse, a positive pulse, and another negative pulse (refer to the right side of FIG. 22).

The system of claim 21, wherein the PFE output from the PFE generator includes a PFE waveform having a repeated pattern to provide a biased energy of positive polarity without muscle contraction, the repeated pattern including single positive pulse, single negative pulse, single positive pulse.

Figure 23:
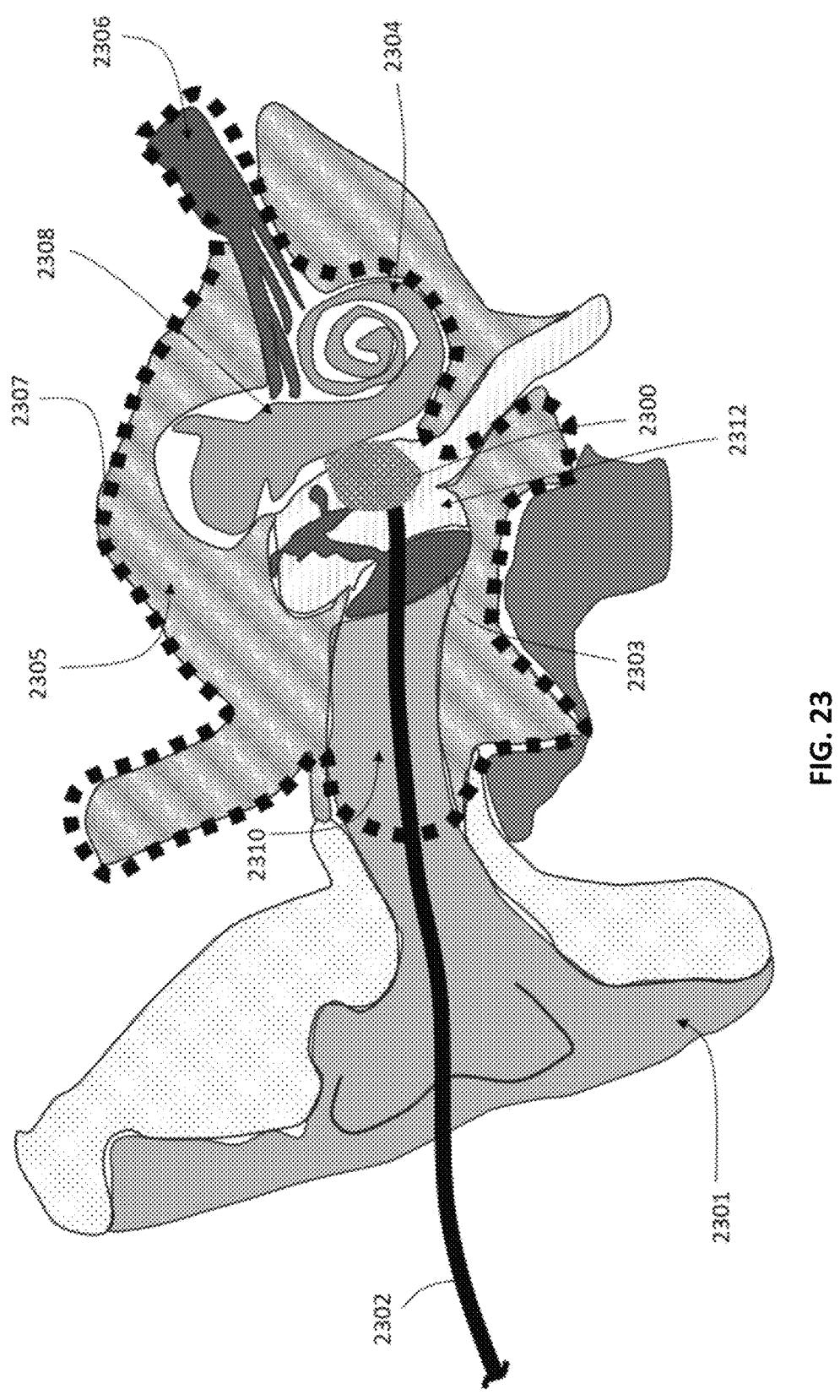
FIG. 23 shows a side view of a distal portion of an example PFE delivery instrument for use in a patient's ear, in accordance with various embodiments.

Referring now to FIG. 23, a PFE delivery instrument (e.g., similar to one or more embodiments of the PFE delivery instrument 200 described in FIGS. 10A-10B and 11A-11B) can include a self-expanding mesh electrode 2300 comprising conductive materials such as nitinol and other materials. This self-expanding mesh electrode 2300 can be used to treat diseased anatomical regions of the car 2301 within a treatment boundary 2307 depicted in FIG. 23. In some cases, self-expanding mesh electrode 2300 can be fixed to a distal end of a delivery shaft 2302. The delivery shaft 2302 can include an internal conductor lead for electrically connecting the—expanding mesh electrode 2300 to a PFE generator (e.g., PFE generator 130 of FIGS. 1-2). In some cases, the delivery shaft 2302 and the self-expanding mesh electrode 2300 are sized so that the self-expanding mesh electrode 2300 can advance through the patient's ear canal 2310, across the tympanic membrane 2303, and into the middle car 2312. In the middle car 2312, the self-expanding mesh electrode 2300 can deliver PFE to a targeted treatment site.

The delivery shaft 2302 can, in some examples, represent an elongated member that resists bending moments so that delivery shaft 2302 is stiff enough to advance through the patient's anatomical passageways. In some cases, delivery shaft 2302 includes an outer sheath and an inner member, the inner member being sized to pass through a lumen of the outer sheath. The inner member, in some embodiments, can move proximally or distally relative to the outer sheath through the lumen defined by the outer sheath. For example, the self-expanding mesh electrode 2300 can be attached to a distal end of the inner member such that self-expanding mesh electrode 2300 can fit within the lumen defined by the outer sheath when the self-expanding mesh electrode 2300 occupies a retracted state. The inner walls of the outer sheath, for example, can maintain the self-expanding mesh electrode 2300 in the retracted state and prevent the self-expanding mesh electrode 2300 from transitioning to the expanded state. This can facilitate delivery through the tympanic membrane (which may optionally be accessed via a small incision that is 1 mm-4 mm (preferably less than 3 mm) such that the tympanic membrane can self-heal after withdrawal of the system from the car canal). When the inner member moves distally relative to the outer sheath, the self-expanding mesh electrode 2300 can pass out of a distal opening of the outer sheath and transition from the retracted state to the expanded state. In embodiments where self-expanding mesh electrode 2300 comprises nitinol, the self-expanding mesh electrode 2300 can automatically expand when it emerges from the outer sheath due to the outer sheath no longer maintaining the self-expanding mesh electrode 2300 in the retracted position.

In some cases, the self-expanding mesh electrode 2300 can occupy a retracted state when advancing through the car canal 2310, across the tympanic membrane 2303, and into the middle car 2312 and the self-expanding mesh electrode 2300 can transition from the retracted state to an expanded state within the middle car 2312 proximate to a targeted treatment site. For example, when the delivery shaft 2302 includes an outer sheath and an inner member attached to the self-expanding mesh electrode 2300, the inner member can move distally relative to the outer sheath so that the self-expanding mesh electrode 2300 exits a distal opening of the outer sheath when the self-expanding mesh electrode 2300 is within the middle car 2312. This can cause the self-expanding mesh electrode 2300 to automatically transition from the retracted state to the expanded state.

In some embodiments, in the retracted state, the self-expanding mesh electrode 2300 can have a diameter that is less than or equal to a diameter of the delivery shaft 2302. For example, in embodiments where delivery shaft 2302 includes an outer sheath and an inner member, the self-expanding mesh electrode 2300 in the retracted state can fit within a lumen defined by the outer sheath so that the diameter of the outer sheath is greater than the diameter of the self-expanding mesh electrode 2300 in the retracted state. This can allow the self-expanding mesh electrode 2300 and delivery shaft 2302 to pass through the car canal 2310 and across the tympanic membrane 2303 (e.g., through a small surgical opening in the tympanic membrane 2303) to reach the middle car 2312.

As described above, the self-expanding mesh electrode 2300 can be attached to a distal end of delivery shaft 2302, which can be advanced through car canal 2310 and across tympanic membrane 2303 to reach the middle car 2312. Within the middle car 2312, self-expanding mesh electrode 2300 can stimulate parts of the patient's anatomy such as the cochlea 2304, mastoid air cells 2305, cochlear nerve fibers 2306 the vestibule 2308, the tympanic membrane 2303, among other anatomy. For example, self-expanding mesh electrode 2300 can deliver PFE proximate to the cochlea 2304 to stimulate cochlear nerve fibers 2306. This delivery of PFE can induce regeneration of the cochlear hair cells. In some examples, PFE can induce a reset of cochlea 2304 by inducing apoptosis to kill diseased tissue surrounding the cochlea so that healthy tissue replaces the diseased tissue. This can promote a health of cochlear hair cells within the cochlea 2304.

In some embodiments, self-expanding mesh electrode 2300 advance within mastoid air cells 2305 so that self-expanding mesh electrode 2300 can eradicate infectious tissue by delivering PFE. The PFE procedure can be delivered as a standalone procedure, but also can be combined with another procedure, where PFE mesh electrode 2300 is activated after the other procedure is completed. For example, drilling of mastoid air cells 2305 can be performed to remove diseased tissue, or open infected mastoid air cells. In some cases, the PFE can be delivered after the mastoid cells are opened to ensure the bacteria and infection is eradicated. If bacteria are trapped within the biofilm, PFE can be used to disrupt the biofilm matrix and kill the bacteria. The self-expanding mesh electrode 2300 can be applied within the tympanic membrane 2303 or within the outer car 2301, including the car canal 2312, for the treatment of chronic otitis externa and chronically infected car canal.

Figure 24:
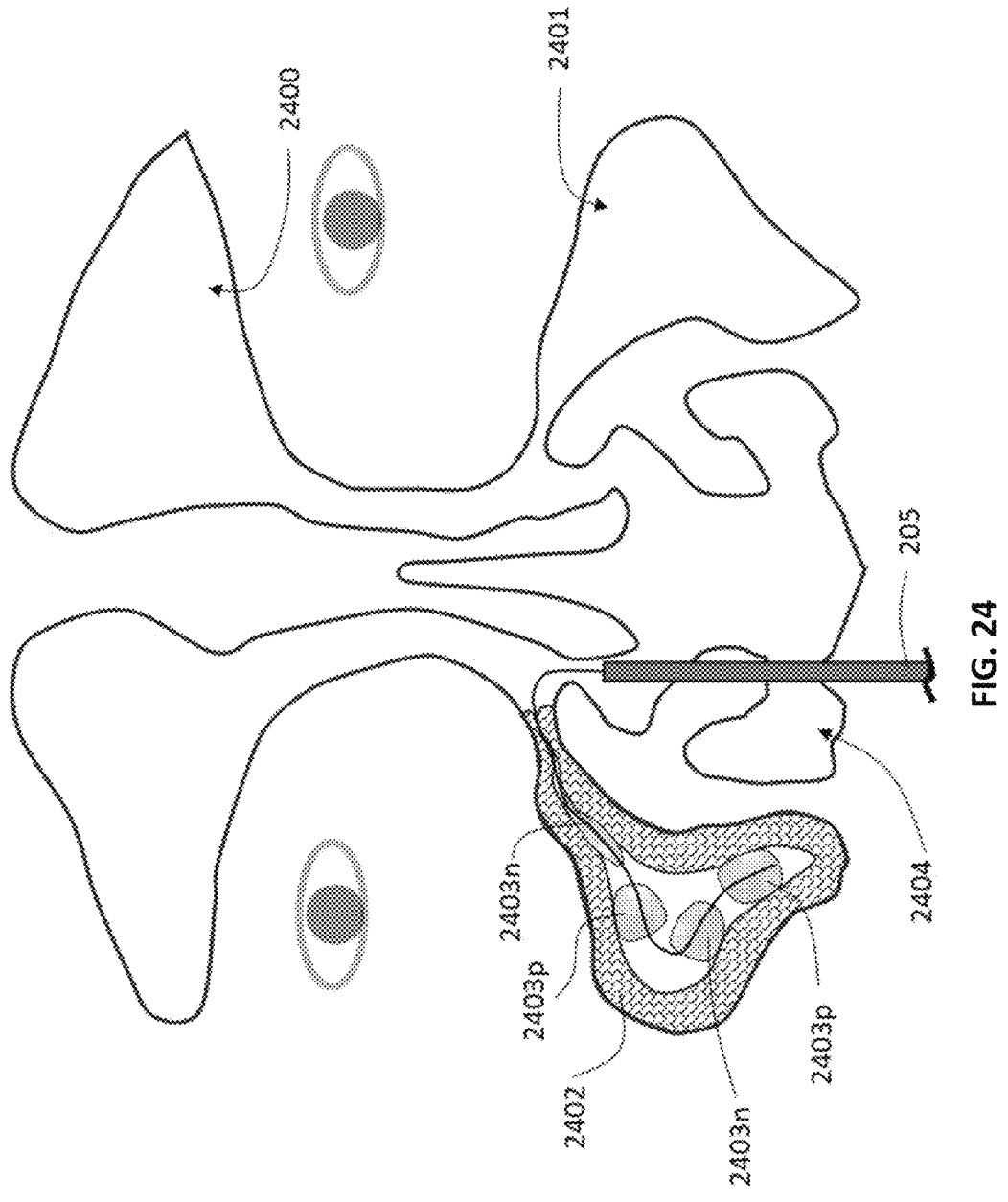
FIG. 24 shows a side view of a distal portion of an example PFE delivery instrument for use in a patient's sinus cavity, in accordance with various embodiments.

Referring now to FIG. 24, a PFE delivery instrument can deliver PFE to targeted tissue such as tissue within frontal sinuses 2400, tissue within maxillary sinuses 2401, and tissue within other anatomical spaces. In some embodiments, similar to the PFE delivery instrument 200 depicted in FIGS. 10A-10B, control console 100 can deliver PFE (e.g., using the PFE generator 130 of FIGS. 1-2) to the PFE delivery instrument 200 depicted in FIG. 24 to treat tissue of the maxillary sinus 2401. Additionally or alternatively, the frontal sinuses 240 depicted in FIG. 24 can be accessed by the PFE delivery instrument 200 so as to deliver PFE treatment the tissue within the frontal sinuses 2400.

In some embodiments, the PFE delivery instrument 200 includes one or more PFE electrodes that can be configured in a way that is similar to the electrodes 211 of FIG. 6C. For example, delivery instrument 200 can include a set of four PFE electrodes 2403a-2403d (collectively, "electrodes 2403") where some of the electrodes 2403 are of positive polarity and some of the electrodes 2403 are of negative polarity. In some embodiments, electrodes 2403a and 2403c can be of positive polarity and electrodes 2403b and 2403d can be of negative polarity. In some embodiments, electrodes 2403a and 2403c can be of negative polarity and electrodes 2403b and 2403d can be of positive polarity. In both of these embodiments, electrodes 2403 can alternate between positive and negative polarity. In some embodiments, some of the electrodes 2403 can be of positive polarity while other ones of the electrodes 2403 are of negative polarity, such that polarities are reversed respectively, to deliver bipolar PFE. In some embodiments, all the electrodes 2403 can be configured to alternate between positive and negative polarity, simultaneously, so the electrodes are synchronized to deliver monopolar PFE.

PFE delivery to paranasal sinuses and specifically frontal sinuses 2400 and maxillary sinuses 2401 can eliminate or significantly reduce mucosal thickening of the sinus. Mucosal thickening can refer to a thickness of a mucous membrane 2402 lining sinus cavities (e.g., a cavity of the maxillary sinuses 2401 as depicted in FIG. 24). In some examples, PFE can reduce inflammation of the mucous membrane 2402 that results from infections, allergies, or chronic sinusitis, resulting in mucosa thickening. By reducing the thickened mucosa, PFE can result in improved airflow through the sinus openings, contributing to improvements or elimination of symptoms such as nasal congestion, facial pain, infection, and pressure, because the PFE treatment within the sinus can propagate into adjacent cavities such as the nasal cavity 2404 which can include an extension of same mucous membrane 2402 that lines the maxillary sinuses 2401.

Figure 25:
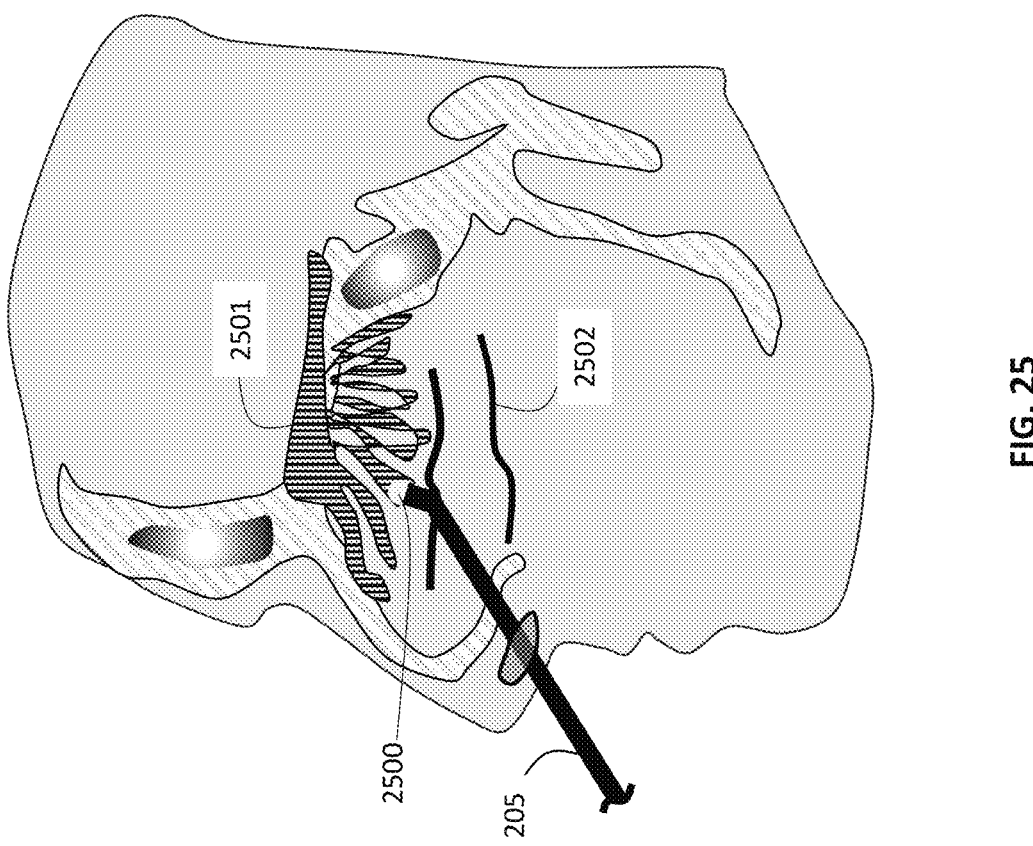
FIG. 25 shows a side view of a distal portion of an example PFE delivery instrument for use in a patent's olfactory system, in accordance with various embodiments.

Referring now to FIG. 25, a distal tip 2500 of an embodiment of PFE delivery instrument 200 can be bent so that a PFE electrode located at distal tip 2500 is directed towards the olfactory system 2501 of a patient. In some examples, the olfactory system 2501 is located superior to the turbinates 2502. Bending distal tip 2500 can bring distal tip 2500 closer to the olfactory system 2501 (e.g., the olfactory bulb) as compared with examples where distal tip 2500 is not bent. Distal tip 2500 of the PFE delivery instrument 200, when generator 130 is activated (as explained in connection with FIGS. 1-2 above), can deliver PFE treatment to targeted tissue in a way that triggers cellular apoptosis, thus replacing faulty cells with healthy cells.

In some examples, PFE delivery instrument 200 includes an actuator mechanism that allows a user to bend the distal tip 2500 of the PFE delivery instrument 200. This actuator mechanism, for example, can include a knob, a switch, a slider, or any other kind of actuator mechanism that causes distal tip 2500 to bend relative to a longitudinal axis of PFE delivery instrument 200. In some cases, PFE delivery instrument 200 can include a pull wire that is attached to a distal end of the PFE delivery instrument 200. This pull wire can cause the distal tip 2500 of PFE delivery instrument 200 to bend when the pull wire is tightened.

In some embodiments, a region of the olfactory system includes faulty cells that can contribute to abnormal nerve activity. This abnormal nerve activity can result in a worsening or complete loss of smell due to neural degeneration, surrounding tissue degeneration, or environmental triggers including strong odors, cold air exposure, alcohol ingestion, and/or spicy foods. Signals generated by the neural network within the olfactory bulb can result in loss of smell, migraines, and/or other conditions. In some embodiments, distal tip 2500 can deliver PFE to replace and regenerate cells through apoptosis and/or stimulate nerves. This can result in neural improvements and restoring of nerves and other tissue within the olfactory system to their normal functioning, thus improving smell, taste, and other conditions such as migraines that might have been caused by abnormal activity of neural signaling and/or other diseased tissue present in this region.

Figure 26:
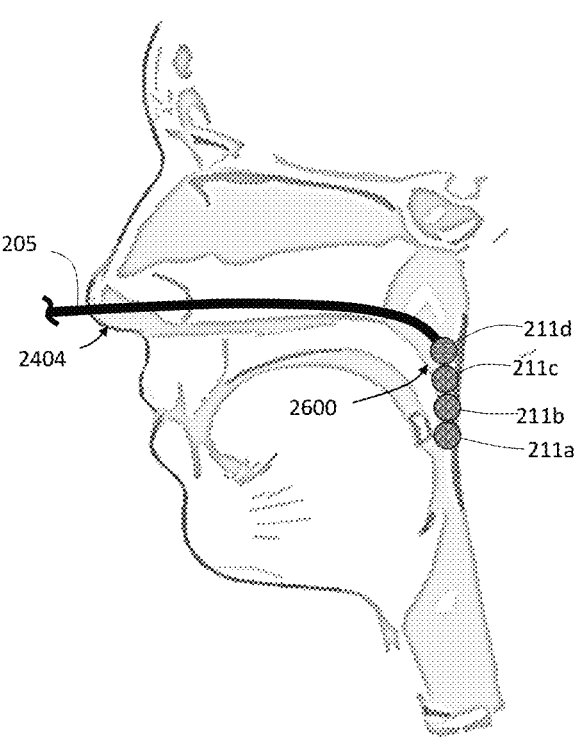
FIG. 26 shows a side view of a distal portion of an example PFE delivery instrument for use in a patent's throat, in accordance with various embodiments.

Referring now to FIG. 26, some embodiments of system 10 involve a PFE delivery instrument 200 including an elongated shaft 205 and a distal tip 204 (e.g., as described in FIGS. 6A-6C) for treating retropalatal, retroglossal, and epiglottis regions of a patient's throat 2600. For example, PFE delivery instrument 200 can be advanced into a throat region where the air flow is obstructed by airway strictures (e.g., a narrowing of airway). When distal tip 204 is proximate to targeted tissue at the throat 2600, PFE delivery instrument 200 can deliver PFE to treat the targeted tissue via one or more PFE electrodes. As depicted in FIG. 26, the PFE delivery instrument 200 can represent an embodiment that includes a set of user-controlled, selectively inflatable balloons (e.g., balloons 211 of FIGS. 6A-6C). The PFE delivery instrument 200 depicted in FIG. 26 can include any of the electrode embodiments depicted in FIGS. 6A-6C (e.g., electrodes 221*a*, 221*b*, 222).

In some examples, the dilation balloons 211 can be used in conjunction with one or more electrodes to dilate the patient's airway stricture and deliver a PFE treatment. In some embodiments, dilation and PFE delivery (e.g., using the PFE generator 130 of FIGS. 1-2) can occur simultaneously. In some embodiments, dilation can occur before PFE delivery. In some cases, other delivery tools can be used, such as a delivery tool including a basket electrode (e.g., the basket electrode 220 of FIGS. 3-4) to provide only PFE therapy without performing dilation so that PFE induces apoptosis in the targeted treatment area to remove dead tissue and stimulates the targeted treatment area to regenerate healthy tissue in place of the dead tissue. In some examples, PFE delivery instrument 200 can treat infectious tissue within the throat 2600. PFE delivery instrument 200 can deliver PFE to targeted tissue to induce the apoptosis in a way that kills bacteria, even when PFE delivery instrument 200 is embedded within a biofilm. This can cause lymphocytes to migrate to the targeted tissue, thus releasing T and B cell types that can fight any remaining bacteria.

In some examples, anatomical regions where PFE is delivered as shown in FIGS. 10A-10B, 23, 24, and 25, can be related to migraine and headache triggers. For example, eliminating diseased tissue within the mastoid, sinus cavity, or olfactory system can provide relief to the patient not only within the anatomical structure(s) where the PFE was delivered, but also provide relief in migraine and headache episodes being reduced or eliminated. In addition to eliminating congestion within nasal, sinus, and other regions of head and neck, headache and migraine episodes can be reduced through delivery of PFE. In some cases, the patient can realize additional relief from a neural interface and ionic channels being modulated and/or reset to normal activity where triggers such as various antigens and pathogens do not initiate a migraine or headache episode. This is because the tissues interfacing with the neural activity can be returned to healthy non-diseased tissues.

It should be understood that any one or more of the teachings, expressions, embodiments, examples, etc. described herein may be combined with any one or more of the other teachings, expressions, embodiments, examples, etc. that are described herein. The embodiments described herein should therefore not be viewed in isolation relative to each other. Various suitable ways in which the teachings herein may be combined will be readily apparent in view of the teachings herein. Such modifications and variations are intended to be included within the scope of the claims.

Having shown and described various embodiments of the present invention, further adaptations of the methods and systems described herein may be accomplished by appropriate modifications without departing from the scope of the present invention. Accordingly, the scope of the present invention should be considered in terms of the following claims and is understood not to be limited to the details of structure and operation shown and described in the specification and drawings.

What is claimed is:

1. A method comprising:

inserting an elongated shaft of a Pulsed Field Electroporation (PFE) delivery instrument into a nose site having targeted nasal tissue such that an adjustable PFE electrode of a treatment tip at a distal end of the PFE delivery instrument is adjacent to the targeted nasal tissue, wherein the elongated shaft defines an inflation lumen that extends through the elongated shaft across an entire axial length of the PFE electrode such that one or more distal sidewall fluid ports of the inflation lumen are located distally of a distal-most end of the PFE electrode;

adjusting the PFE electrode relative to the elongated shaft by delivering an inflation fluid through the inflation lumen that extends across the entire axial length of the PFE electrode so as to compress the PFE electrode against the targeted nasal tissue, the inflation fluid being delivered through said one or more distal sidewall fluid ports of the inflation lumen located distally of the distal-most end of the PFE electrode, through one or more proximal sidewall fluid ports of the inflation lumen located proximally of a proximal-most end of the PFE electrode, and through one or more intermediate sidewall fluid ports of the inflation lumen located between of the distal-most end of the PFE electrode and the proximal-most end of the PFE electrode, wherein the inflation lumen extends distally beyond said one or more distal sidewall fluid ports;

activating a PFE generator of a control console connected to the PFE delivery instrument to output, via a conductor connected to the PFE electrode, an electric field in a predefined pattern from the PFE electrode to induce at least one of irreversible electroporation (IRE) at the targeted nasal tissue and reversible electroporation (RE) at the targeted nasal tissue, wherein the conductor is located within a conductor lumen that extends through the elongated shaft to a conductor sidewall opening that is proximal to the PFE electrode, and wherein the conductor passes through the conductor sidewall opening and extends distally from the conductor sidewall opening and along a surface of the treatment tip to connect to the PFE electrode at a connection point, the conductor extending distally along the surface of the treatment tip between the conductor sidewall opening and the connection point, an entire length of the conductor between the sidewall opening and the connection point located radially outward of the surface of the treatment tip.

2. The method of claim 1, further comprising, in response to receiving a communication at the control console indicating that the PFE delivery instrument is authorized for use, adjusting the PFE generator from a disabled state to an enabled state.

3. The method of claim 1, wherein the PFE delivery instrument includes a handle, the elongated shaft extending distally from the handle, and the treatment tip at a distal end portion of the elongated shaft with a dilation balloon and the adjustable PFE electrode.

4. The method of claim 3, further comprising contemporaneously dilating the targeted nasal tissue while outputting PFE treatment from the PFE electrode compressed against the targeted nasal tissue.

5. The method of claim 3, wherein the PFE delivery instrument includes a unique identifier affixed to an exterior surface that is readable by the control console.

6. The method of claim 5, further comprising capturing the unique identifier using a user interface of the control console.

7. The method of claim 6, further comprising modifying characteristics of a PFE output from the PFE electrode in response to the control console detecting a type of the PFE delivery instrument from the captured unique identifier.

8. The method of claim 3, wherein the handle of the PFE delivery instrument includes a PFE activation button to selectively activate the PFE electrode to output PFE treatment.

9. The method of claim 1, further comprising delivering a fluid drug through at least one fluid drug delivery lumen of the elongated shaft in communication with at least one drug delivery port at the treatment tip of the PFE delivery instrument such that the treatment tip is contemporaneously delivers PFE treatment from the PFE electrode at the targeted nasal tissue and a fluid drug at the targeted nasal tissue, each fluid drug delivery lumen of the at least one fluid drug delivery lumen extending through the elongated shaft across an entire axial length of the PFE electrode, wherein each fluid drug delivery lumen of the at least one fluid drug delivery lumen comprises a fluid drug delivery sidewall opening located proximal to the one or more proximal sidewall fluid ports of the inflation lumen, the fluid drug delivery sidewall opening being in fluid communication with the at least one drug delivery port at the treatment tip of the PFE delivery instrument for said delivering the fluid drug.

10. The method of claim 1, wherein said inserting comprises inserting the elongated shaft of the PFE delivery instrument into the nose site, and the PFE delivery instrument comprises a nasal dilation instrument having a handle, the elongated shaft extending distally from the handle, and the treatment tip at a distal end portion of the elongated shaft with a dilation balloon and the adjustable PFE electrode.

11. The method of claim 10, wherein said adjusting the PFE electrode comprises inflating, by delivering the inflation fluid through the inflation lumen, the dilation balloon of the nasal dilation instrument so that the nasal tissue is dilated by the dilation balloon and the PFE electrode is compressed against the nasal tissue, the inflation lumen in fluid communication with the dilation balloon via the one or more distal sidewall fluid ports, the one or more intermediate sidewall fluid ports, and the one or more proximal sidewall fluid ports located inside of the dilation balloon, wherein at least a portion of the entire length of the conductor extending between the conductor sidewall opening and the connection point extends along a surface of the dilation balloon at a location radially outward of the dilation balloon, and wherein the conductor sidewall opening is proximal to the dilation balloon.

12. The method of claim 11, wherein said activating the PFE generator provides delivery of PFE from the treatment tip at the nasal tissue dilated by the dilation balloon.

13. The method of claim 10, wherein the control console is configured to receive a connector of the nasal dilation instrument, the PFE control console including a user interface display and the PFE generator configured to output the electric field in the predefined pattern from the PFE electrode via the conductor extending through the connector.

14. The method of claim 13, wherein the nasal dilation instrument includes a unique identifier affixed to the connector that is readable by the control console.

15. The method of claim 14, wherein the PFE generator is maintained in a disabled state and, in response to the control console capturing the unique identifier of the nasal dilation instrument to confirm the nasal dilation instrument is an authorized instrument, the control console adjusts the PFE generator into an enabled state.

16. The method of claim 10, wherein the handle of the nasal dilation instrument includes a PFE activation button to selectively activate the PFE electrode at the treatment tip of the nasal dilation instrument.

17. The method of claim 10, wherein the inflation lumen is in fluid communication with an interior of the dilation balloon via the one or more distal sidewall fluid ports, the one or more proximal sidewall fluid ports, and the one or more intermediate sidewall fluid ports, and wherein the method further comprises delivering, via a drug delivery sidewall opening of a fluid drug delivery lumen extending through the elongated shaft across an entire axial length of the PFE electrode, a fluid drug or agent to the nasal tissue from one or more pores in an outer balloon disposed outward from the dilation balloon, the drug delivery sidewall opening located proximal to the one or more proximal sidewall fluid ports of the inflation lumen, and the fluid drug delivery lumen in fluid communication with a space between the outer balloon and the dilation balloon via the drug delivery sidewall opening for said delivering the fluid drug or agent.

18. The method of claim 17, wherein the drug delivery sidewall opening is located proximal to the dilation balloon and distal to a location where a proximal end of the outer balloon attaches to the elongated shaft.

19. The method of claim 10, further comprising contemporaneously delivering a fluid drug or agent to the nasal tissue from at least one drug delivery port at the treatment tip of the dilation balloon while the electric field is output from the PFE electrode at the treatment tip of the dilation balloon.

20. The method of claim 19, wherein the elongated shaft includes at least one fluid drug delivery lumen in communication with the at least one drug delivery port at the treatment tip of the nasal dilation instrument such that the treatment tip is configured to contemporaneously dilate the nasal tissue, deliver PFE treatment from the PFE electrode at the nasal tissue, and deliver a fluid drug or agent to the nasal tissue, each fluid drug delivery lumen of the at least one fluid drug delivery lumen extending through the elongated shaft across an entire axial length of the PFE electrode.

21. The method of claim 1, wherein at every point along the entire length of the conductor between the sidewall opening and the connection point, the conductor represents the outward-most extent of the treatment tip at the distal end of the PFE delivery instrument.

22. The method of claim 1, wherein the inflation lumen comprises a greater number of intermediate sidewall fluid ports than proximal sidewall fluid ports, and wherein the inflation lumen comprises a greater number of intermediate sidewall fluid ports than distal sidewall fluid ports.

23. The method of claim 1, wherein the conductor sidewall opening is proximal to a most proximal one of the one or more proximal sidewall fluid ports.

* * * * *